(12) United States Patent
Brewer et al.

(10) Patent No.: US 12,268,501 B2
(45) Date of Patent: Apr. 8, 2025

(54) ALL-IN ONE SYRINGE ASSEMBLY FOR BLOOD DRAWS AND MEDICINE DELIVERY TO PATIENTS

(71) Applicants: Michael Brewer, Irvine, CA (US); Robert Fortune, Claremont, CA (US); Bill Phillips, Irvine, CA (US)

(72) Inventors: Michael Brewer, Irvine, CA (US); Robert Fortune, Claremont, CA (US); Bill Phillips, Irvine, CA (US)

( * ) Notice: Subject to any disclaimer, the term of this patent is extended or adjusted under 35 U.S.C. 154(b) by 493 days.

(21) Appl. No.: 17/112,790

(22) Filed: Dec. 4, 2020

(65) Prior Publication Data

US 2021/0085230 A1 Mar. 25, 2021

Related U.S. Application Data

(62) Division of application No. 16/872,265, filed on May 11, 2020, now abandoned.

(60) Provisional application No. 62/909,669, filed on Oct. 2, 2019, provisional application No. 62/845,767, filed on May 9, 2019.

(51) Int. Cl.
*A61B 5/15* (2006.01)
*A61B 5/154* (2006.01)

(52) U.S. Cl.
CPC .... *A61B 5/150236* (2013.01); *A61B 5/15003* (2013.01); *A61B 5/150244* (2013.01); *A61B 5/150389* (2013.01); *A61B 5/150519* (2013.01); *A61B 5/150572* (2013.01); *A61B 5/154* (2013.01)

(58) Field of Classification Search
CPC .......... A61B 5/150236; A61B 5/15003; A61B 5/150244; A61B 5/150389; A61B 5/150519
See application file for complete search history.

(56) References Cited

U.S. PATENT DOCUMENTS

| 5,137,511 | A | * | 8/1992 | Reynolds | A61M 5/284 604/416 |
| 8,394,068 | B2 | * | 3/2013 | Kosinski | A61M 5/31511 604/219 |
| 8,992,505 | B2 | * | 3/2015 | Thorne, Jr. | A61M 5/31596 604/184 |
| 2012/0150129 | A1 | * | 6/2012 | Jin | A61M 39/10 285/332 |
| 2013/0338631 | A1 | * | 12/2013 | Butlin | A61M 5/19 604/506 |
| 2018/0042539 | A1 | * | 2/2018 | Woloschuk | A61B 5/150717 |

(Continued)

*Primary Examiner* — Daniel L Cerioni
(74) *Attorney, Agent, or Firm* — FisherBroyles, LLP; Rob L. Phillips

(57) ABSTRACT

A syringe assembly includes (i) a syringe with a cylindrical body, luer tip at a first end, finger grip at a second end and a cannula extending from the luer tip into the cylindrical body, and (ii) a plunger unit having an adapter portion, receiving cavity, finger grip and piston. A channel extends the length of the adapter portion to receive the cannula in one end and a variety of connectors, valves and/or syringes in a second end. The end of the channel accessible in the receiving cavity mates with or engages any number of commercially available valves, connectors and/or syringes while the luer tip similarly connects to any number of valves, catheters, connectors, etc., depending on the task being undertaken with the syringe assembly.

17 Claims, 24 Drawing Sheets

(56) References Cited

U.S. PATENT DOCUMENTS

2018/0221578 A1* 8/2018 Hopkins .......... A61B 5/150351
2018/0318572 A1* 11/2018 Kraus ................... A61M 5/162
2019/0125978 A1* 5/2019 Daily .................. A61M 5/3272

* cited by examiner

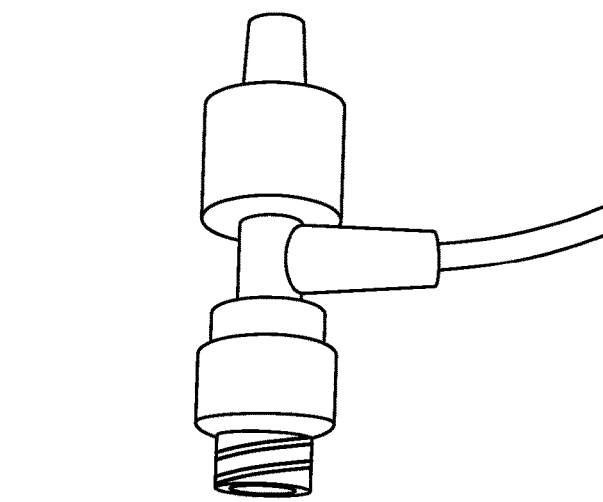
FIG. 7
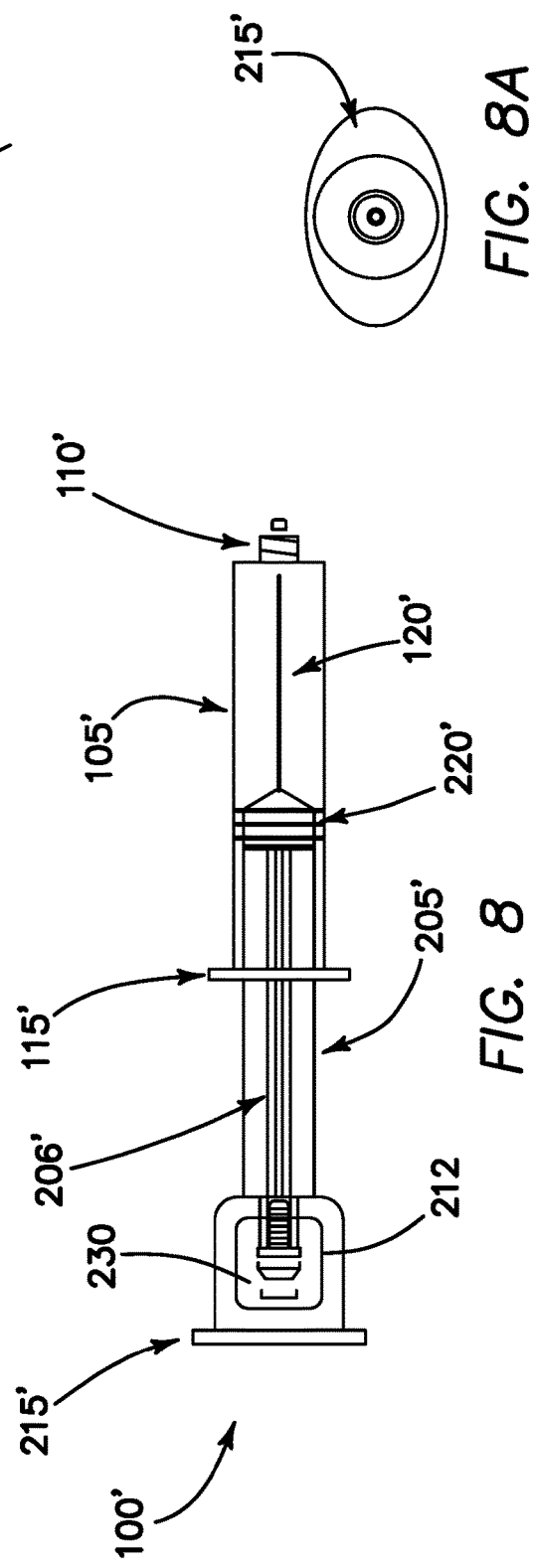
FIG. 8A
FIG. 8

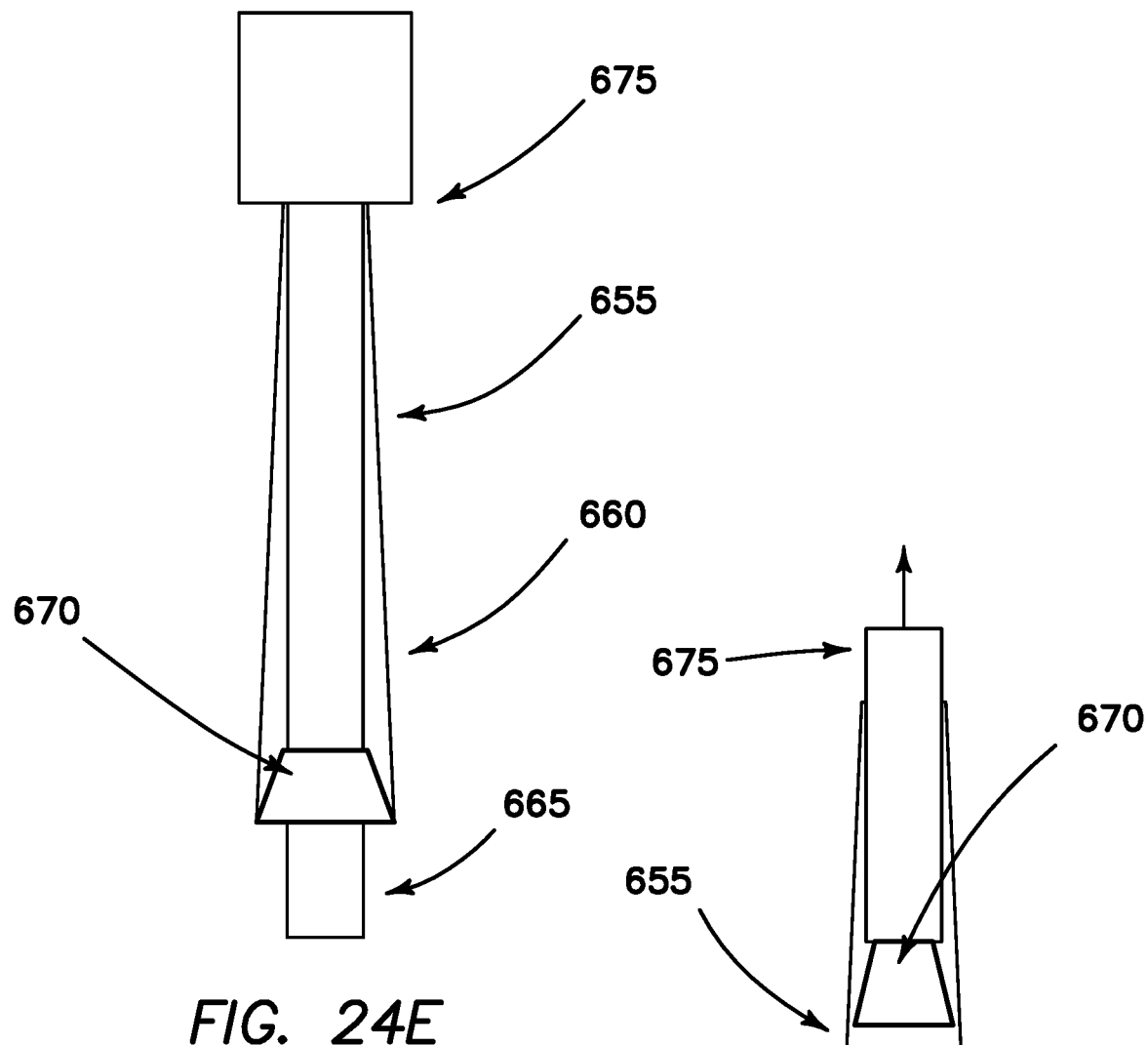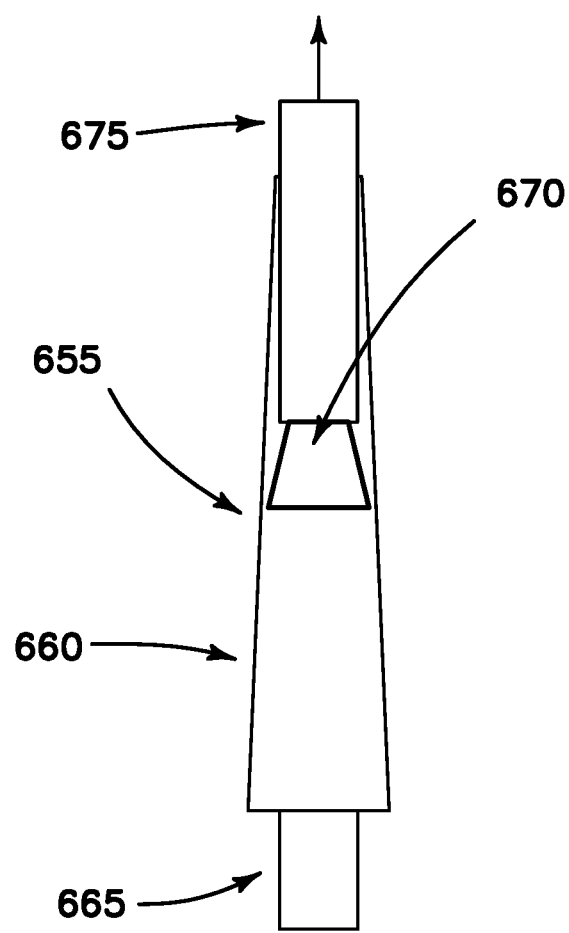
FIG. 24E
FIG. 24F

ALL-IN ONE SYRINGE ASSEMBLY FOR BLOOD DRAWS AND MEDICINE DELIVERY TO PATIENTS

CROSS-REFERENCE

This application is a division of and claims priority to U.S. patent application Ser. No. 16/872,265 filed May 11, 2020 which claims priority to U.S. Provisional Application No. 62/845,767 filed May 9, 2019, and U.S. Provisional Application No. 62/909,669, filed Oct. 2, 2019 the contents of each incorporated herein by reference.

FIELD OF THE INVENTION

The embodiments of the present invention relate generally to medical syringe assembly for withdrawing fluid from a patient and injecting medicines into a patient whereby the syringe is configured to (i) minimize contamination and hemolysis in the fluids; (ii) reduce time needed to undertake tasks; and (iii) reduce items needed to undertake tasks.

BACKGROUND

Blood samples for testing may be collected from patients using many devices. Many such collections currently utilize a syringe including a cylindrical body and a plunger assembly. The cylindrical body has an interior wall, an open proximal end, a closed distal end, and a distal opening through the distal end. A hypodermic needle or indwelling catheter may be provided on, or attached to, the distal end communicating with the distal opening.

Unfortunately, the current syringes having cylindrical bodies and plunger assemblies suffer from drawbacks, including unsatisfactory (i) connector performance and adaptability; (ii) cannula position and attachment; (iii) plunger design; and (iv) related design shortcomings.

Thus, it would be advantageous to develop a syringe having a cylindrical body and a plunger assembly which overcomes the noted drawbacks. Furthermore, it would be advantageous to develop such a syringe that can be pre-filled with a medicine or flush as needed.

SUMMARY

The embodiments of the present invention first include a syringe having a generally cylindrical body with a first end for mating to a connector and a second, spaced open end for receipt of a plunger unit. A finger grip extends radially outward from the second open end. In one embodiment, the finger grip is a pair of oppositely extending flanges formed integrally with the syringe. A cannula extends from the first end to a point within the cylindrical body near the second open end.

The embodiments of the present invention next include a plunger unit adapted to slidably insert into the cylindrical body of the syringe. An adapter portion of the plunger unit is slidably disposed in the cylindrical body of the syringe. A piston on the end of the adapter portion of the plunger unit sealably engages an interior wall of the cylindrical body thereby defining a dynamic fluid chamber between an aft surface of the piston and an inner surface of the first end of the cylindrical body. A channel in the adapter portion of the plunger unit receives the second end of the cannula. A second portion of the plunger unit comprises a receiving cavity. In one embodiment, the receiving cavity is a generally cylindrical body extending from, and integral with, the adapter portion of the plunger unit. A finger grip may extend radially outward from an open end of the receiving cavity. In one embodiment, the diameter of the receiving cavity is greater than the diameter of the syringe so as to receive numerous different devices including vacutainers.

A needle-free valve is positioned partially within the plunger unit channel and extends into the receiving cavity. The needle-free valve serves to seal the channel from the retrograde flow of air and may engage a specimen tube, syringe or other device. The valve may take on many forms and purposes as detailed below.

As configured, the adapter portion of the plunger unit is free to move within the cylindrical body of the syringe as guided by the piston and cannula. Friction created by the piston engaging the cylindrical body of the syringe provides slight resistance against movement of the plunger unit and maintains the plunger unit in place when no external force is applied. Locking mechanisms may be incorporated to lock the plunger unit relative to the syringe into which it is inserted.

Other variations, embodiments and features of the present invention will become evident from the following detailed description, drawings and claims.

BRIEF DESCRIPTION OF THE DRAWINGS

FIG. 7 illustrates a syringe assembly with a locking blunt cannula adaptor according to the embodiments of the present invention;

FIGS. 8 and 8A illustrate side and top views of a first alternative receiving cavity design according to the embodiments of the present invention;

FIG. 20C illustrates a third view of a syringe assembly with a cannula within a cannula design according to the embodiments of the present invention;

FIG. 24E illustrates a tapered cylindrical syringe body acting as a plunger unit lock according to the embodiments of the present invention;

FIG. 24F illustrates the tapered cylindrical syringe body with the plunger unit moved according to the embodiments of the present invention;

DETAILED DESCRIPTION

Figures 1, 2:
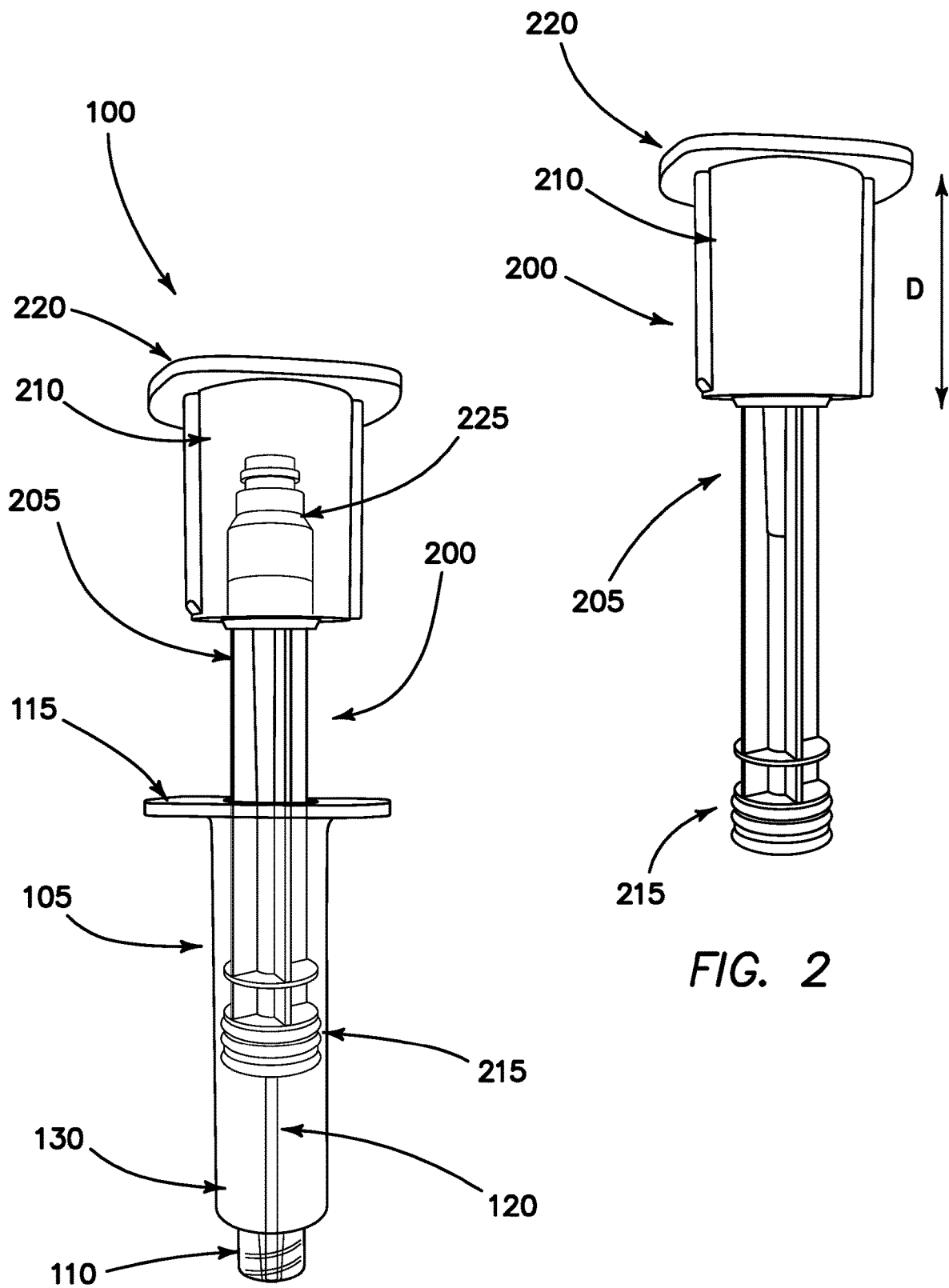
FIG. 1 illustrates one embodiment of a syringe assembly according to the embodiments of the present invention.
FIG. 2 illustrates one embodiment of a plunger unit according to the embodiments of the present invention.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

The individual parts of the syringe assembly may be fabricated of any suitable materials including but not limited to polymers, alloys, metals, composites and combinations thereof. The individual parts of the syringe assembly may be fabricated using any suitable manufacturing techniques, including but not limited to molding, casting, additive printing, forming and combinations thereof.

FIG. 1 shows one embodiment of a syringe assembly 100 according to the embodiments of the present invention. In general, the syringe assembly 100 includes (i) a syringe 105 comprising a cylindrical body, luer tip 110 at a first end, finger grip 115 at a second end and a cannula 120 extending from the luer tip 110 into the cylindrical body, and (ii) a plunger unit 200 comprising an adapter portion 205, receiving cavity 210, finger grip 215 and piston 220.

As shown in FIG. 1, a valve 225 engages one end of a channel 206 extending the length of the adapter portion 205. In one embodiment, the channel 206 is tapered along its length in a decreasing manner from the receiving cavity 210 to the cannula 120. The second end of the channel 206 receives the cannula 120. As shown herein, the end of the channel 206 accessible in the receiving cavity 210 accommodates any number of commercially available valves depending on the task being undertaken with the syringe assembly 100.

Figure 2A:
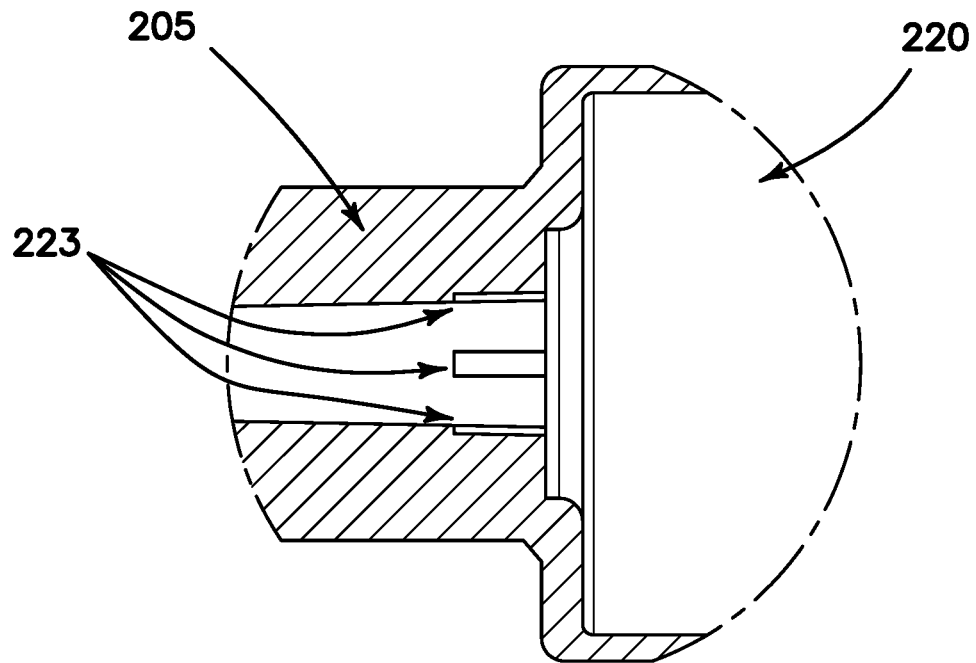
FIG. 2A illustrates a cross-sectional view of a plunger unit with glue slots according to the embodiments of the present invention.
Figure 2B:
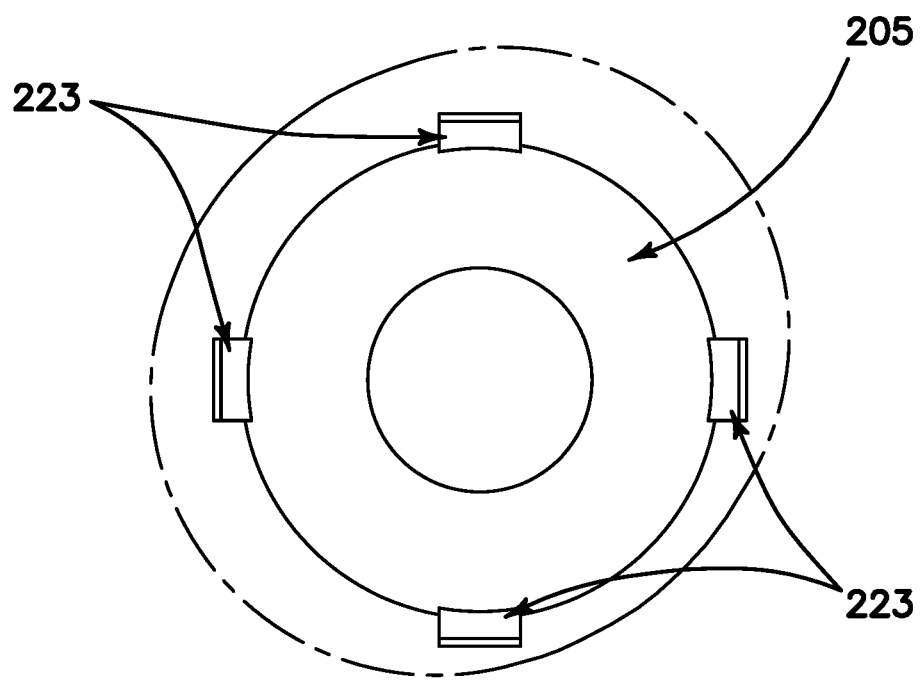
FIG. 2B illustrates an end view of the plunger unit with glue slots according to the embodiments of the present invention.
Figure 3:
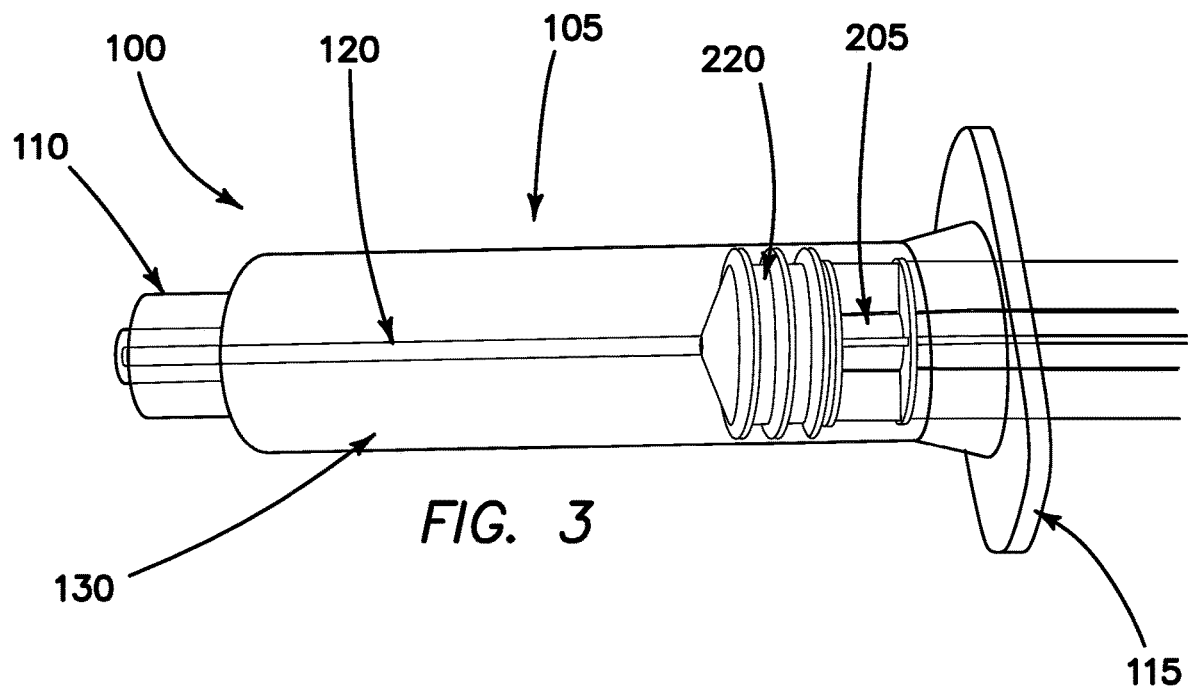
FIG. 3 illustrates a side view of one embodiment of a syringe according to the embodiments of the present invention.
Figure 4:
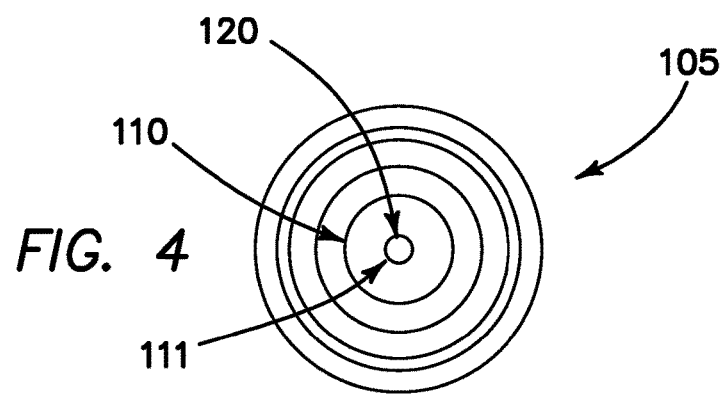
FIG. 4 illustrates an end view of the first end of the syringe of FIG. 3 according to the embodiments of the present invention.
Figure 5:
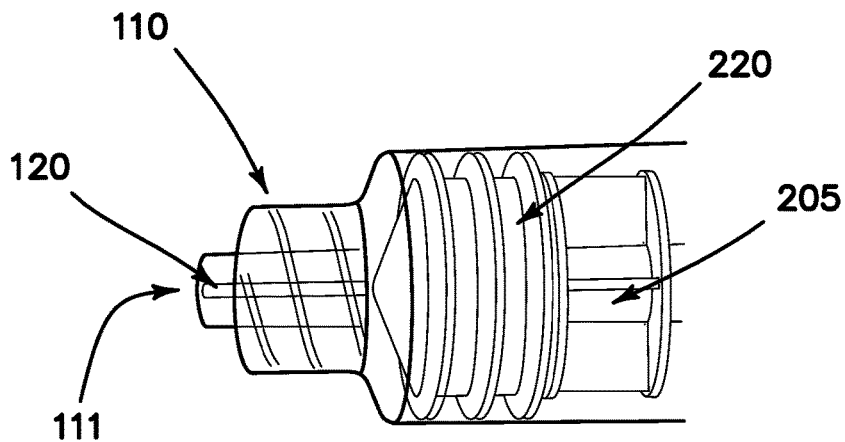
FIG. 5 illustrates the first end of the syringe of FIG. 3 with a cannula in position according to the embodiments of the present invention.

FIG. 2 shows the plunger unit 200 disengaged from the syringe 105. In one embodiment, the adapter portion 205, receiving cavity 210 and finger grip 215 are a single integral item. For example, the adapter portion 205, receiving cavity 210 and finger grip 215 may be collectively fabricated using a single mold. Alternatively, the adapter portion 205, receiving cavity 210 and finger grip 215 may be fabricated individually and thereafter connected to one another. In one embodiment, the adapter portion 205 has an X-cross-section comprising four equally spaced ribs extending the length of the adapter portion 205. In one embodiment, the depth (D) of the receiving cavity 210 is between about 1 inch to about 1.5 inches permitting easy access to any valve (e.g., closed luer valve) engaged with the end of the channel 206 within the receiving cavity 210. In one embodiment, the valve attaches in the channel 206 in the receiving cavity 210 by means of a friction fit. Alternatively, the valve may be adhered to the receiving cavity at the channel 206 using adhesive, such as glue. FIGS. 2A and 2B show glue slots 223 for receipt of glue to attach a valve to the plunger unit 200. In one embodiment, the glue slots 223 have a range of dimensions of about 0.010"-0.250"×005"-0.015"×005"-0.050". In one embodiment, surfaces are EDM finished or acid etched to desired depths and to roughen the surface.

In one embodiment, piston 220 is fabricated of Santoprene 8281-55MED or similar material to create enough seal with the inner surface of the cylindrical body of the syringe 105 preventing push back of fluid.

Figure 6A:
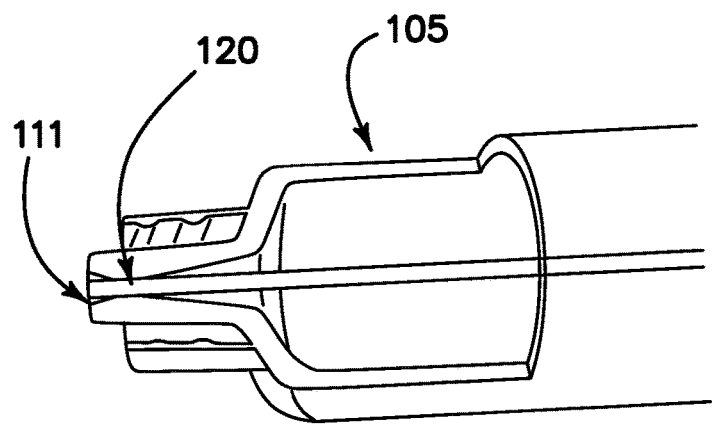
FIG. 6A illustrates the syringe of FIG. 3 with a cut-away area to freely observe the cannula extending into the first end of the syringe according to the embodiments of the present invention.

FIGS. 3 through 6A show the syringe assembly 100 according to the embodiments of the present invention. The syringe assembly 100 incorporates a cannula 120 extending substantially flush with an exit opening 111 in luer tip 110. FIG. 6A shows a cut-away view clearly depicting the position of the cannula 120 substantially flush with the opening 111 at the luer tip 110.

In one embodiment, the cannula 120 is recessed rearward of the opening in the luer tip 110. The recess provides the syringe assembly 100 compatibility with certain connectors, namely needlefree connectors, luer-activated valves and IV connectors which may have an internal spike or similar projection intended to insert into the luer tip 110 for functionality. Examples are the Clave® or MicroClave® made by ICU Medical, Inc., Invision Plus® made by Rymed and OneLink® made by Baxter. Such devices connect to various peripherally inserted central catheters, central lines and peripheral lines. By recessing the cannula 120, space is available to accommodate the spike or similar projection in the luer tip 110. In one embodiment, the cannula 120 is recessed between about 0.15 inches to about 0.35 inches from the opening 111 in the luer tip 110.

Figure 6B:
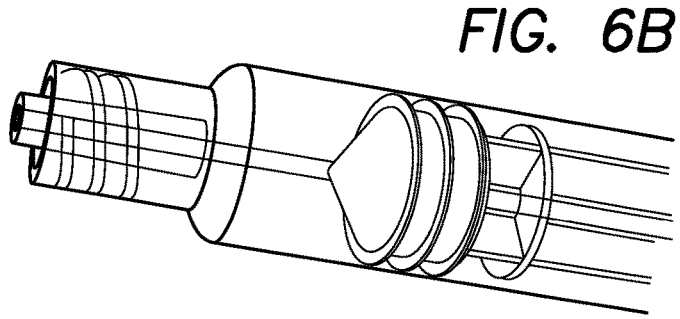
FIG. 6B illustrates a syringe with a recessed cannula according to the embodiments of the present invention.
Figure 6C:
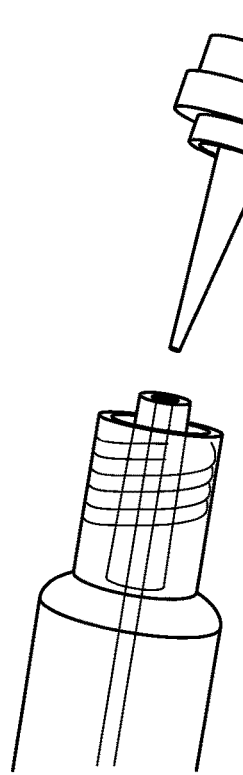
FIG. 6C illustrates the syringe of FIG. 6B proximate a connector with a spike according to the embodiments of the present invention.
Figure 6D:
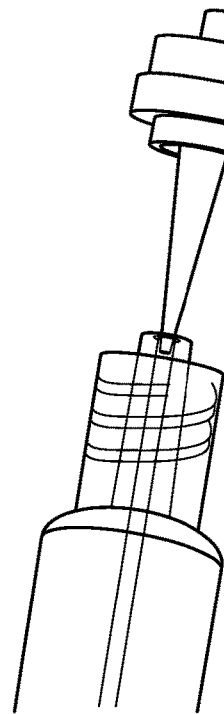
FIG. 6D illustrates the syringe of FIG. 6B mated with the connector of FIG. 6C according to the embodiments of the present invention.

FIGS. 6B-6D show a syringe 102 of the type used with the embodiments of the present invention. In this instance, syringe 102 has a recessed cannula 122 as best seen in FIG. 6B. A connecter 126 having a spike 128 is shown proximate the syringe 102 in FIG. 6C and inserted into the syringe 102 in FIG. 6D. Without the recessed cannula 122, connector 126 would not be able to mate with syringe 102 and function with the corresponding syringe assembly.

The cannula 120 has a cross-section smaller than the opening 110 at the tip thereby allowing fluid to flow between the outer surface of the cannula 120 and the inner surface of the opening into the fluid chamber 130 defined by an aft surface of the piston 220 and an inner surface of the luer end of the syringe 105. In one embodiment, the cannula 120 is secured to the luer tip 110 via one or more flanges, struts, wings, beveled flange, net fit or other mechanical structures (not shown) extending between the inner surface of the luer tip 110 and the outer surface of the cannula 120. The one or more flanges, struts or other mechanical structures should not impede the flow of fluids extending between the inner surface of the luer tip 110 and the outer surface of the cannula 120. In another embodiment, the cannula 120 is secured to the luer tip 110 using self-curing adhesives, UV curing, thermal bonding or may be molded in place, insert molded or over molded or otherwise bonded. Those skilled in the art will recognize that the cannula 120 may be attached to the inner surface of the luer tip 110 using any means available as long it does not interfere with the operation of the syringe assembly 100 as described herein. As used herein, "secured" does not equate to unmovable, as a certain amount of over pressure can cause the cannula 120 to dislodge from the luer tip.

In one embodiment, the syringe 105 incorporates a luer tip 110 is fabricated to comply with ISO Luer Standard 80369-7. ISO 80369-7 is specifically for small-bore connectors intended to be used as intravascular connections in intravascular applications or hypodermic connections in hypodermic applications of medical devices and related accessories such as syringe 105. The luer tip 110 and thread is configured to cooperate with connectors having center post designs and locking and non-locking cannula adaptors. FIG. 7 shows the syringe assembly 100 with a locking blunt cannula adaptor 150 attached according to the embodiments of the present invention. The locking blunt cannular adaptor 150 allows the syringe assembly to access pre-slit connector designs.

Figure 9:
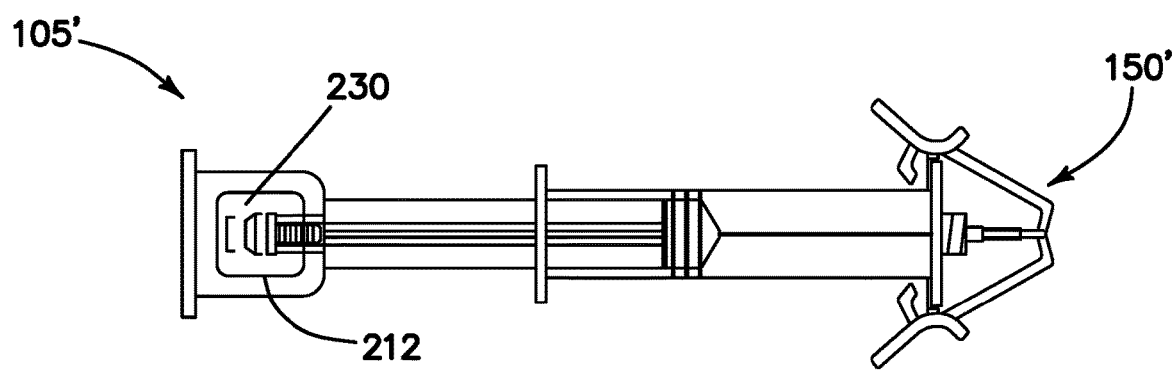
FIG. 9 illustrates the first alternative receiving cavity design with a locking blunt cannula adaptor in place according to the embodiments of the present invention.
Figure 10:
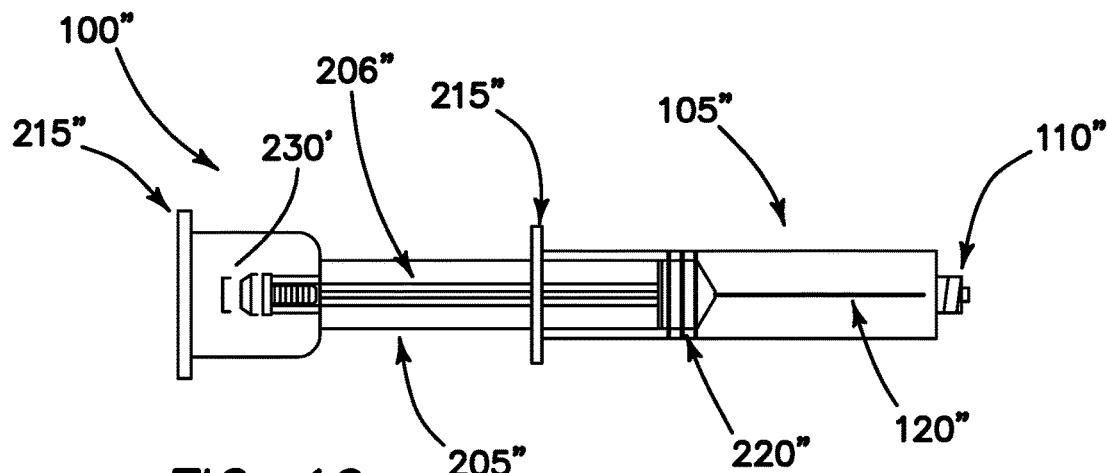
FIGS. 10 and 10A illustrate side and top views of a second alternative receiving cavity design according to the embodiments of the present invention.
Figure 10A:
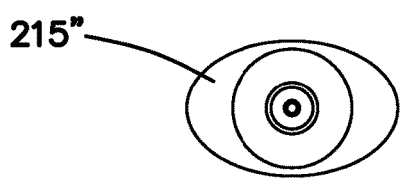
Figure 11:
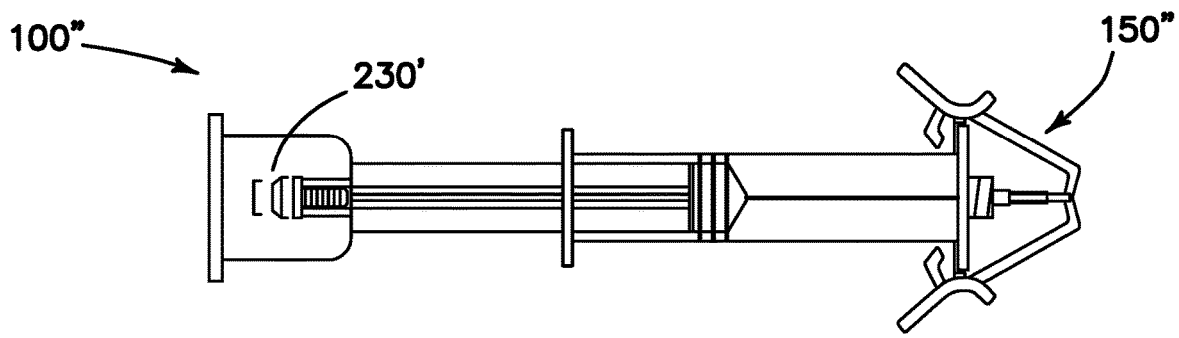
FIG. 11 illustrates the second alternative receiving cavity design with a locking blunt cannula adaptor in place according to the embodiments of the present invention.
Figure 12:
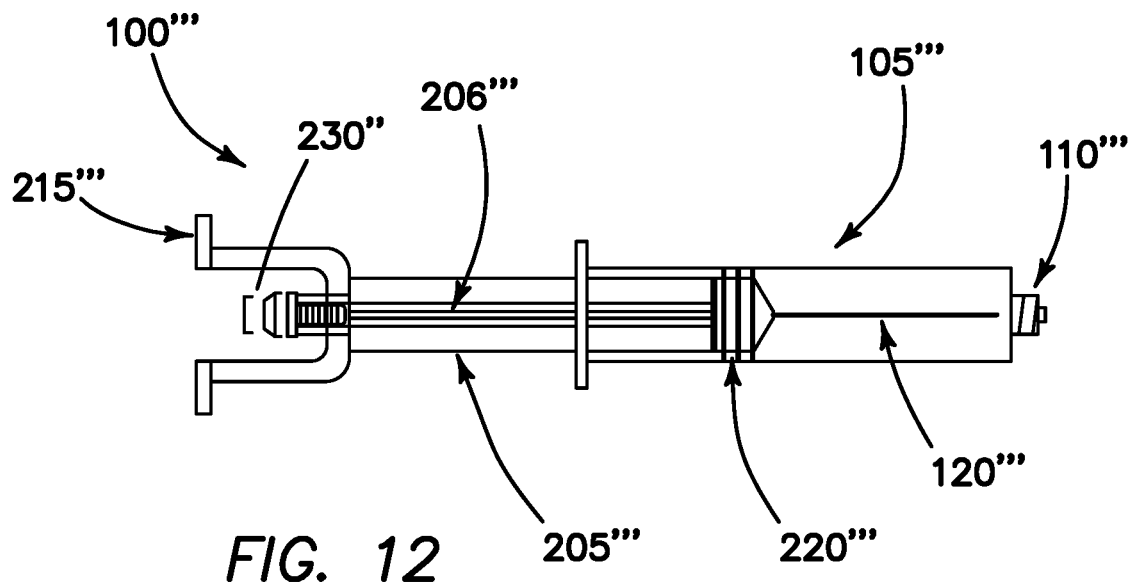
FIGS. 12 and 12A illustrate side and top views of a third alternative receiving cavity design according to the embodiments of the present invention.
Figure 12A:
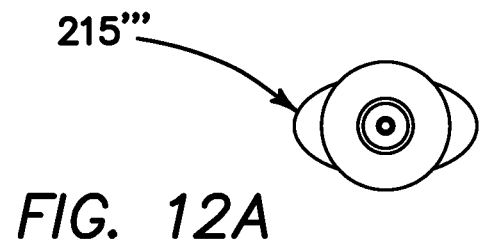
Figure 13:
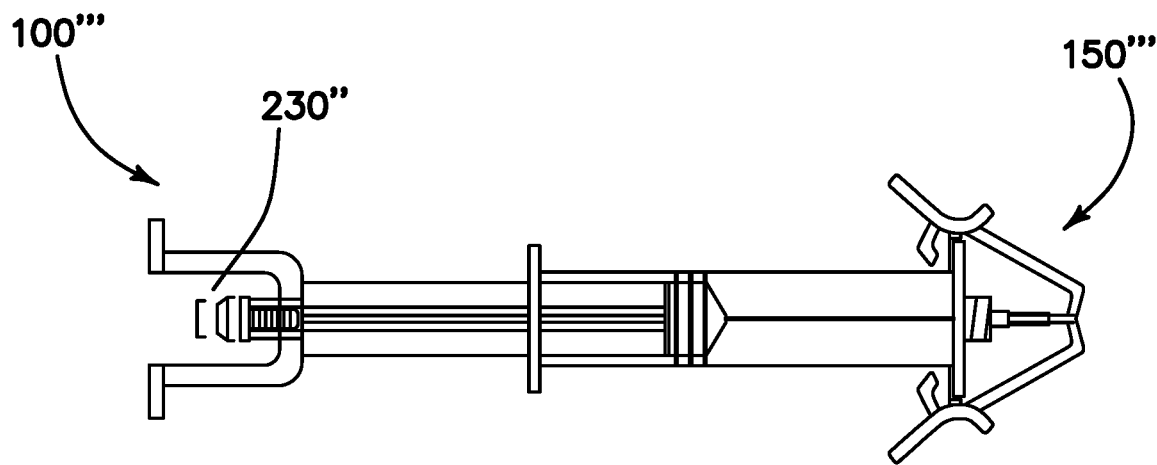
FIG. 13 illustrates the third alternative receiving cavity design with a locking blunt cannula adaptor in place according to the embodiments of the present invention.

FIGS. 8-13 show various embodiments of a syringe assembly having a closed luer valve in place of an open luer valve. FIG. 8 shows a syringe assembly 100' including (i) a syringe 105' comprising a cylindrical body, luer tip 110' at a first end, finger grip 115' at a second end and a cannula 120' extending from the luer tip 110' into the cylindrical body, and (ii) a plunger unit 200' comprising an adapter portion 205', receiving cavity 210' with channel 206', finger grip 215' and piston 220'. The syringe assembly 105' further incorporates a closed luer valve 230 and window 212 in the receiving cavity 210. FIG. 10 shows a syringe assembly 100" including (i) a syringe 105" comprising a cylindrical body, luer tip 110" at a first end, finger grip 115" at a second end and a cannula 120" extending from the luer tip 110" into the cylindrical body, and (ii) a plunger unit 200" comprising an adapter portion 205", receiving cavity 210", finger grip 215" and piston 220". The syringe assembly 105" further incorporates a closed luer valve 230'. FIG. 12 shows a syringe assembly 100''' including a (i) a syringe 105''' comprising a cylindrical body, luer tip 110''' at a first end, finger grip 115''' at a second end and a cannula 120''' extending from the luer tip 110''' into the cylindrical body, and (ii) a plunger unit 200''' comprising an adapter portion 205''', receiving cavity 210''', finger grip 215''' and piston 220'''. The syringe assembly 105''' further incorporates a closed luer valve 230'''. FIGS. 9, 11 and 13 show syringe assemblies 105', 105'' and 105''' with a blunt cannula locking adapter 150' 150'' and 150''' in place.

Figure 14:
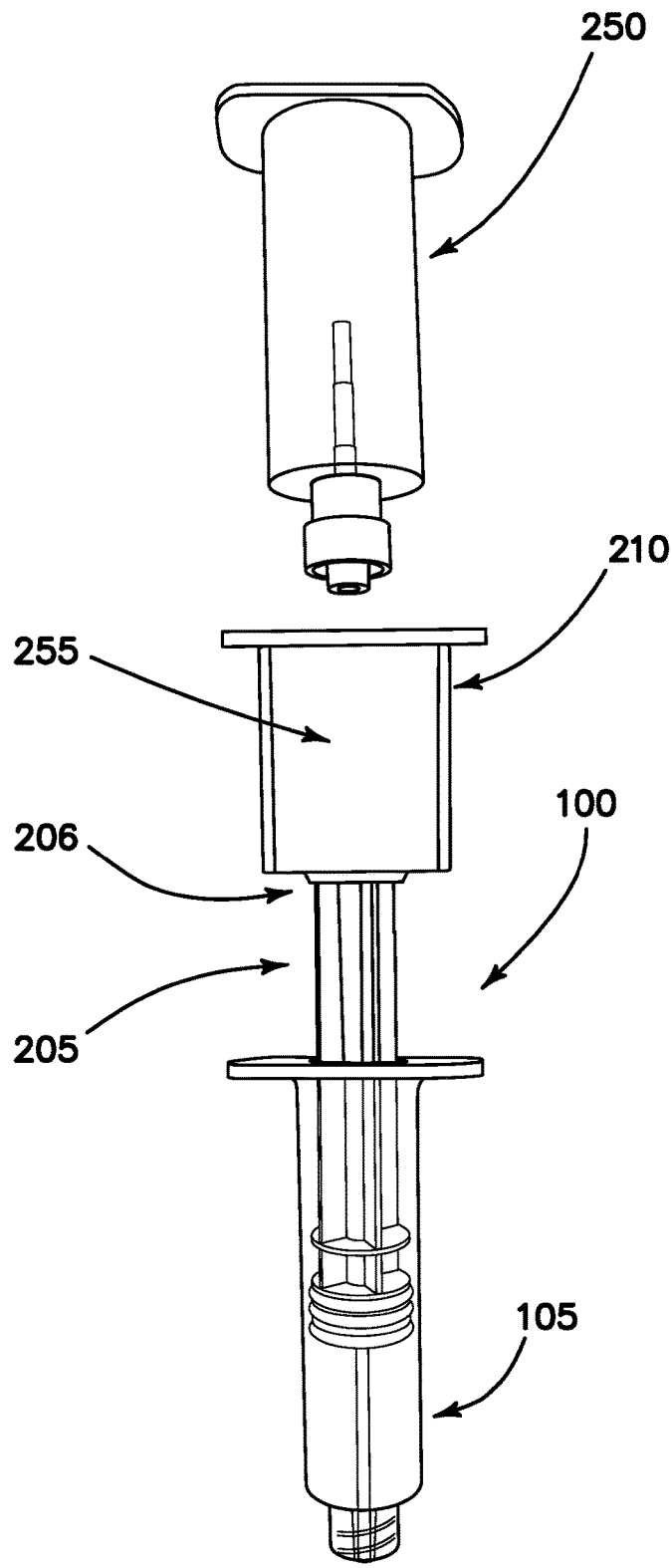
FIG. 14 illustrates one embodiment of the syringe assembly connected to a vacutainer housing according to the embodiments of the present invention.
Figure 15:
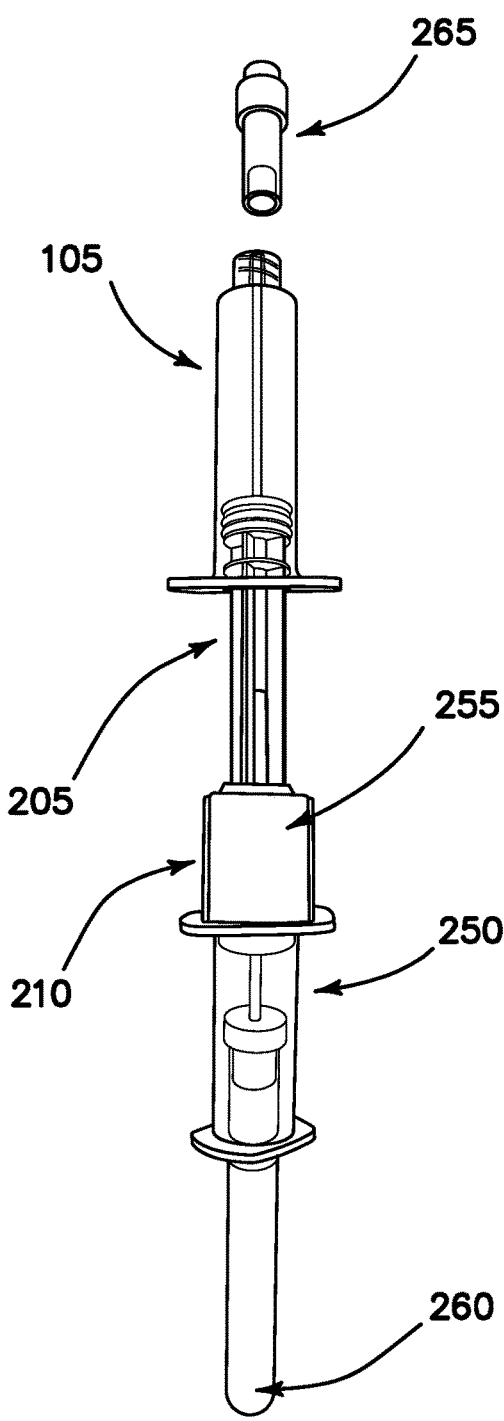
FIG. 15 illustrates one embodiment of the syringe assembly connected to a collection vile according to the embodiments of the present invention.
Figure 16:
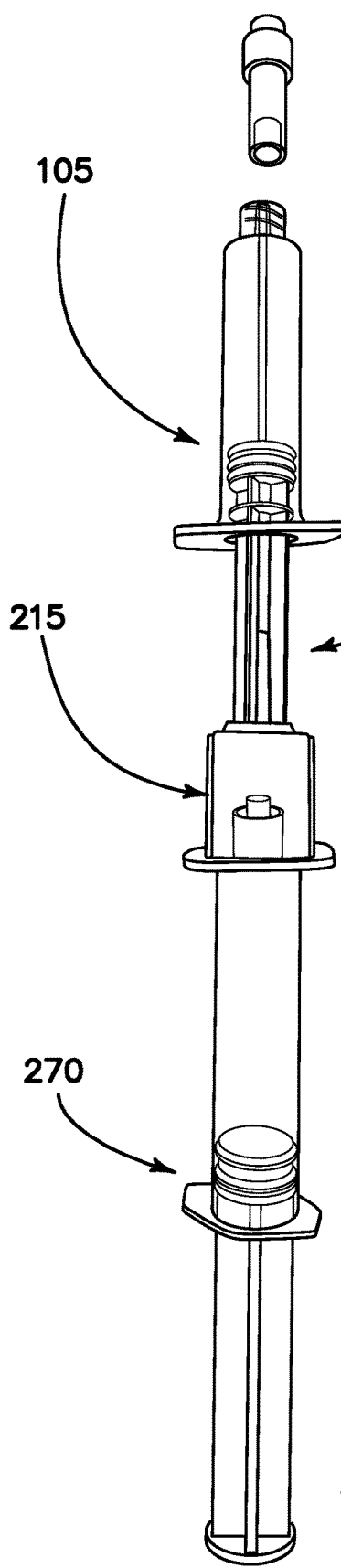
FIG. 16 illustrates one embodiment of the syringe assembly connected to a flush syringe according to the embodiments of the present invention.

FIG. 14 shows syringe assembly 100 positioned for receipt of a vacutainer housing 250 into receiving cavity 110 where valve 255, engaged with channel 206, connects to the vacutainer housing 250. FIG. 15 shows the vacutainer housing 250 in place via attachment to valve 255 and a collection vile 260 inserted into the vacutainer housing 250. An access port 265 is also shown attached to the luer tip 110 for facilitating a blood draw via a PICC line or like device. FIG. 16 shows syringe assembly 100 with a flush syringe 270 attached directly to the channel 206 to allow flushing of the line.

Figure 17:
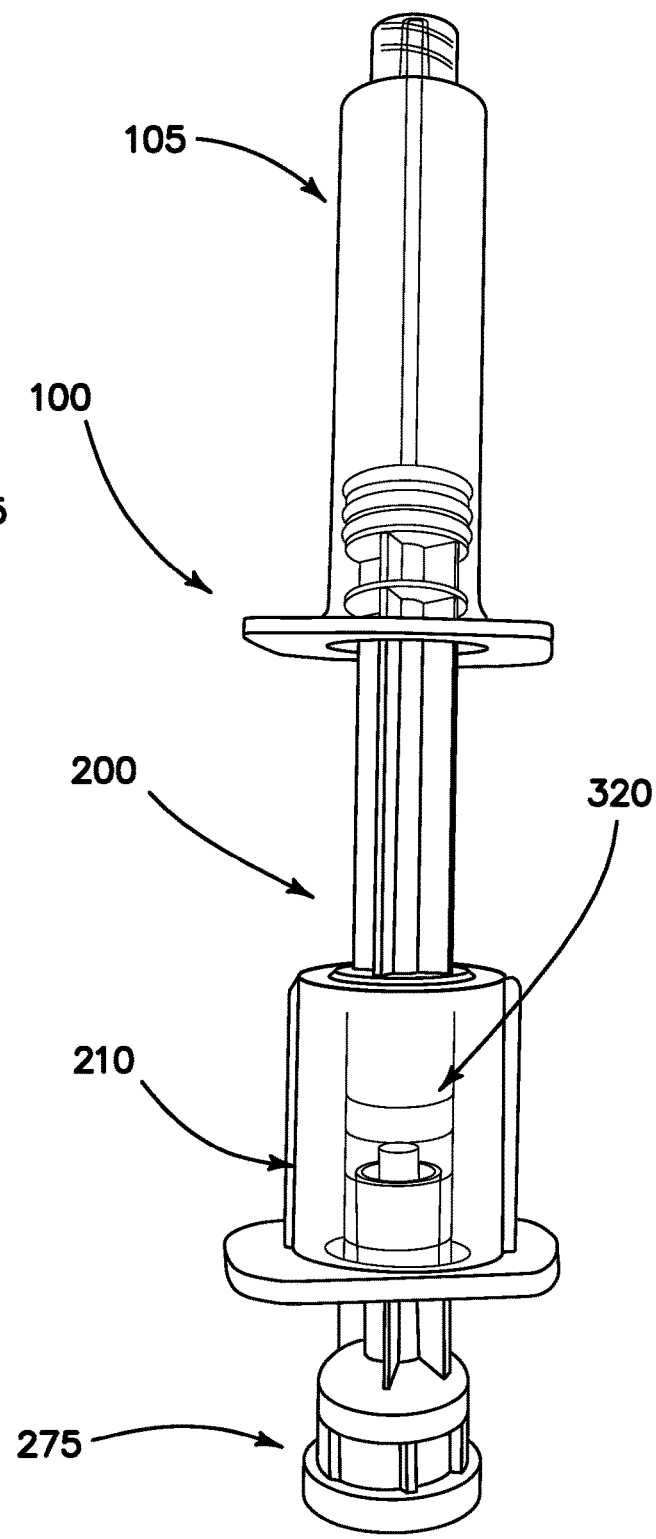
FIG. 17 illustrates one embodiment of the syringe assembly connected to a PhaSeal™ connector according to the embodiments of the present invention.
Figure 18:
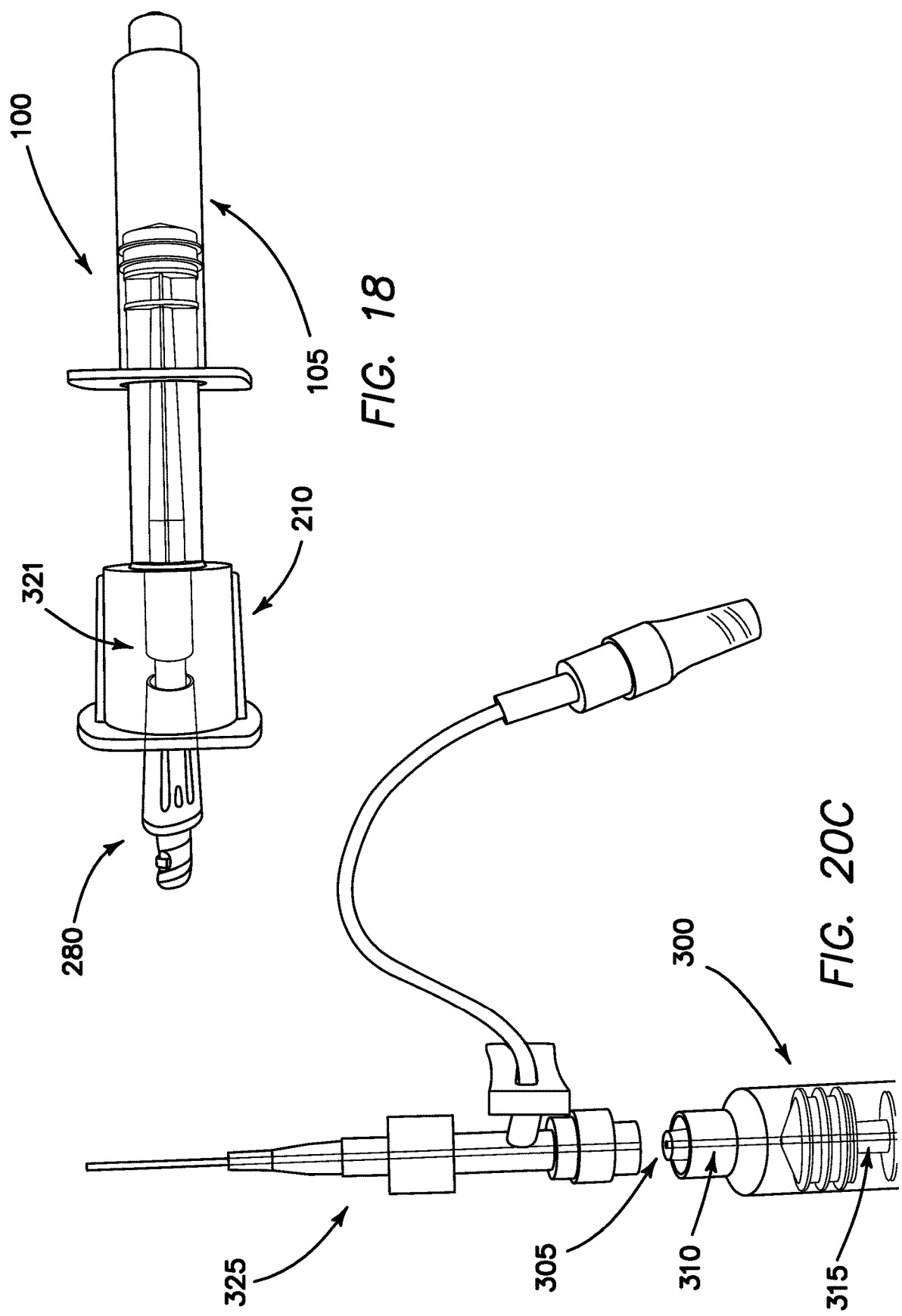
FIG. 18 illustrates one embodiment of the syringe assembly connected to a Texium™ connector according to the embodiments of the present invention.
Figure 19:
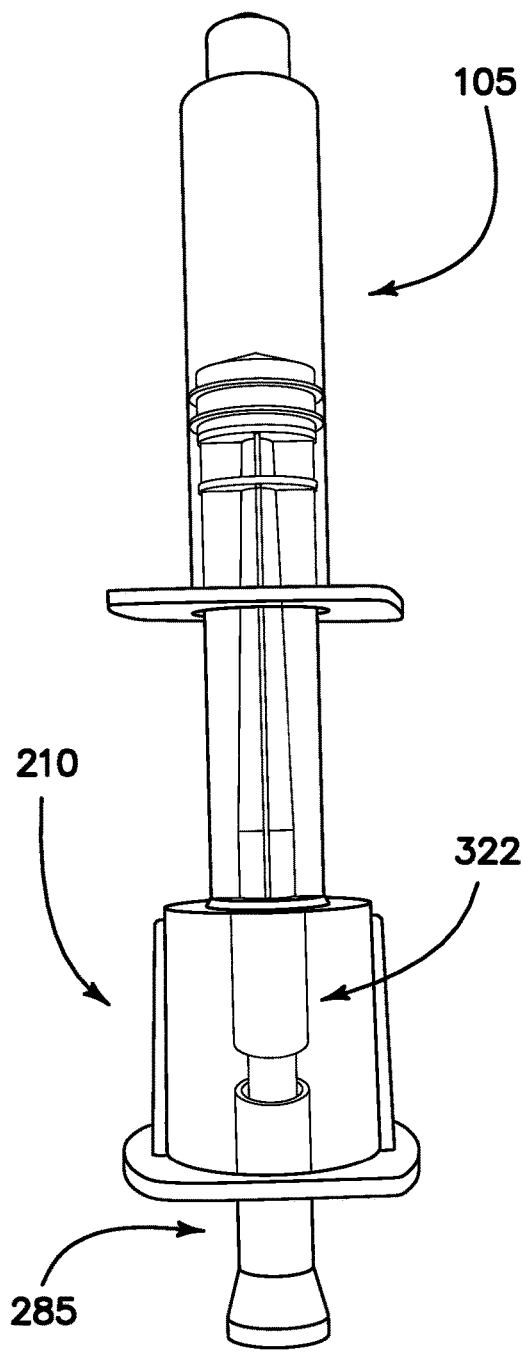
FIG. 19 illustrates one embodiment of the syringe assembly connected to a Spiros™ connector according to the embodiments of the present invention.

FIG. 17 shows the syringe assembly 100 having valve 320 (inside the receiving cavity 210) connected to a PhaSeal™ connector 275 from BD (aka Becton, Dickinson and Company). FIG. 18 shows the syringe assembly 100 having valve (inside the receiving cavity 210) 321 connected to a Texium™ connector 280 from BD. FIG. 19 shows the syringe assembly 100 having valve 322 (inside the receiving cavity 210) connected to a Spiros™ connector 285 from ICU Medical.

Figure 20A:
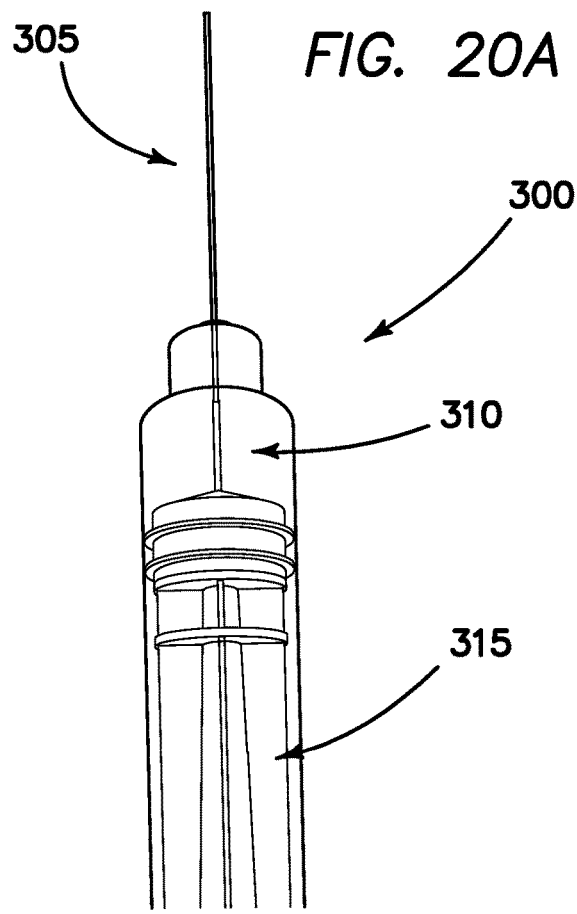
FIG. 20A illustrates a first view of a syringe assembly with a cannula within a cannula design according to the embodiments of the present invention.
Figure 20B:
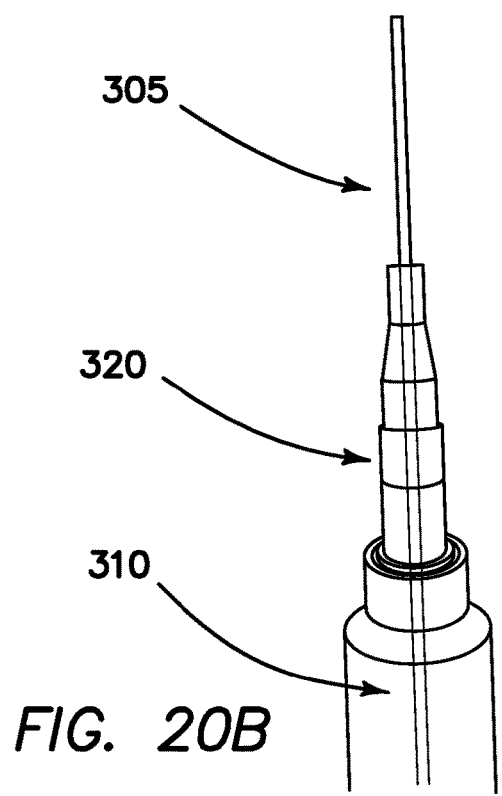
FIG. 20B illustrates a second view of a syringe assembly with a cannula within a cannula design according to the embodiments of the present invention.

FIGS. 20A-20C illustrate a syringe 300 with a cannula 305 within a cannula 310 design according to the embodiments of the present invention. In this embodiment, cannula 305 is positioned within secured cannula 310 and attached to the plunger unit 315. When the plunger unit 315 is depressed cannula 305 advances into and through, for example, a patient's IV peripheral catheter and into the vein. In one embodiment, pre-filled saline/solution acts and aids in the insertion process as the saline/solution "floats" the advancing cannula 305 into the catheter and vein. In such an embodiment, as the plunger unit 315 is depressed, the internal cannula 305 is advanced while simultaneously the plunger unit 315 infuses fluid from the syringe with the internal cannula 305 as it enters the vein. This may also be accomplished by utilizing a saline syringe attached to a valve in the receiving cavity of the plunger unit. Once the successful placement of the internal cannula 305 is achieved, a vacutainer with vacuum tubes or a syringe can be attached to the valve for blood or fluid sampling. Once sampling is concluded, a flush syringe can be attached to the valve for flushing per facility protocol. Once a final flush is completed, the cannula 305 is retracted into cannula 310 or encapsulated into an expandable housing by manual, mechanical, pressure and/or vacuum assist. FIG. 20B shows the cannula 305 inserted into a catheter 320 while FIG. 20C shows the cannula 305 relative to a catheter 325.

Figure 21A:
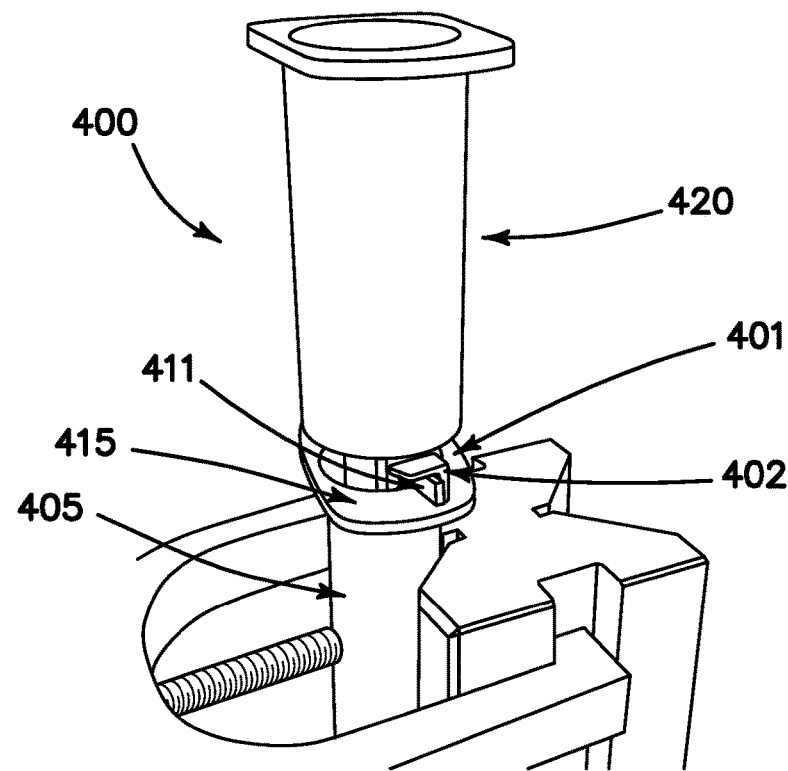
FIG. 21A illustrates a first view of a syringe assembly with a locking mechanism according to the embodiments of the present invention.
Figure 21B:
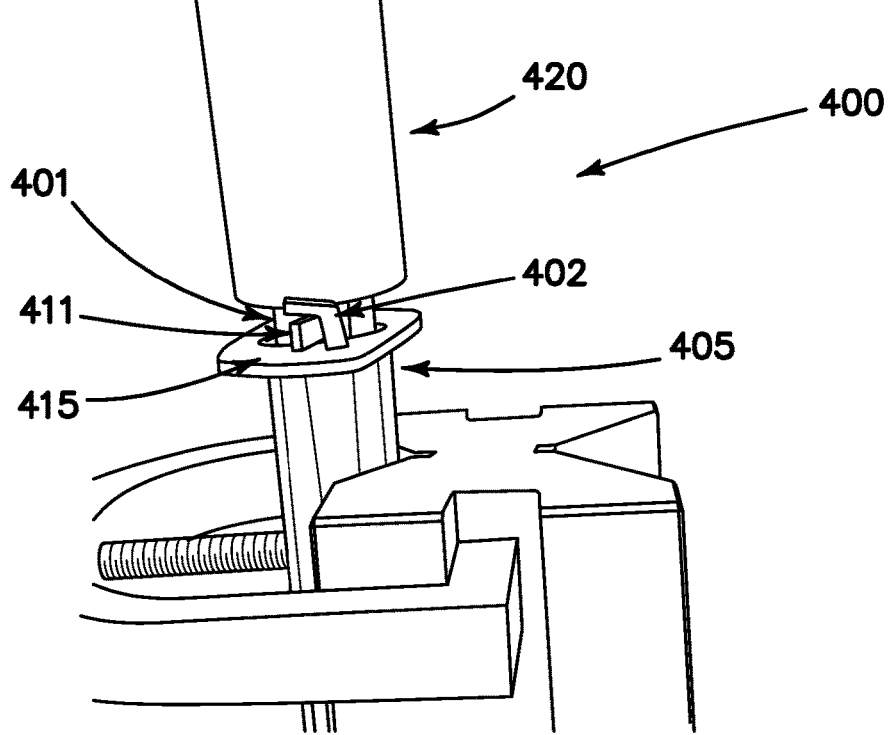
FIG. 21B illustrates a second view of a syringe assembly with a locking mechanism according to the embodiments of the present invention.

FIGS. 21A-21B illustrate a syringe assembly 400 with a locking mechanism 401 according to the embodiments of the present invention. The locking mechanism 401 serves to maintain plunger unit 410 in place at various positions relative to the syringe 405. The locking mechanism 401 also serves to maintain the plunger unit 410 in a fully retracted position. In this embodiment, one or more raised catches 402 on a finger grip 415 of the syringe 405 capture one or more outward extending flanges 411 on the adapter portion 406 of the plunger unit 410 when the plunger unit 410 is rotated at the appropriate position within the syringe 405 locking the plunger unit 410 in place. In one embodiment, the syringe assembly 400 may have flanges 411 extending from opposite sides and the syringe finger grip 415 which has two raised catches 420 positioned, so that when the plunger unit 410 is rotated, the two flanges 411 are captured by the two raised catches 420.

Figure 22A:
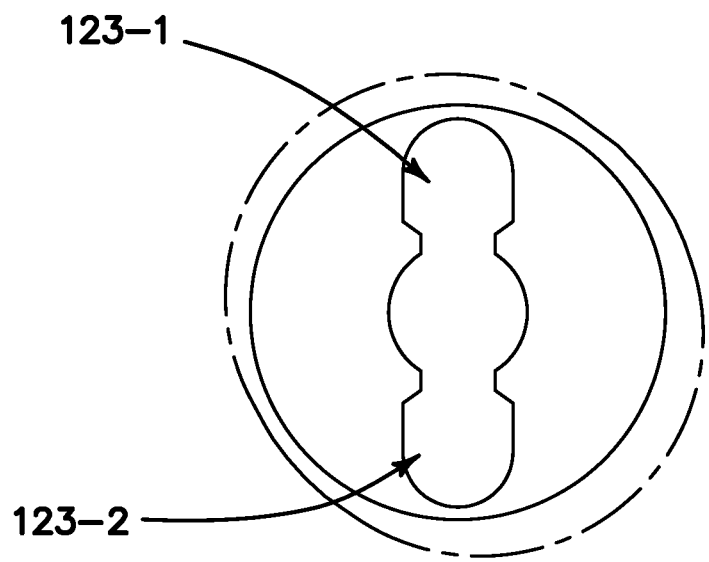
FIG. 22A illustrates an end view of the syringe showing side ports according to the embodiments of the present invention.
Figure 22B:
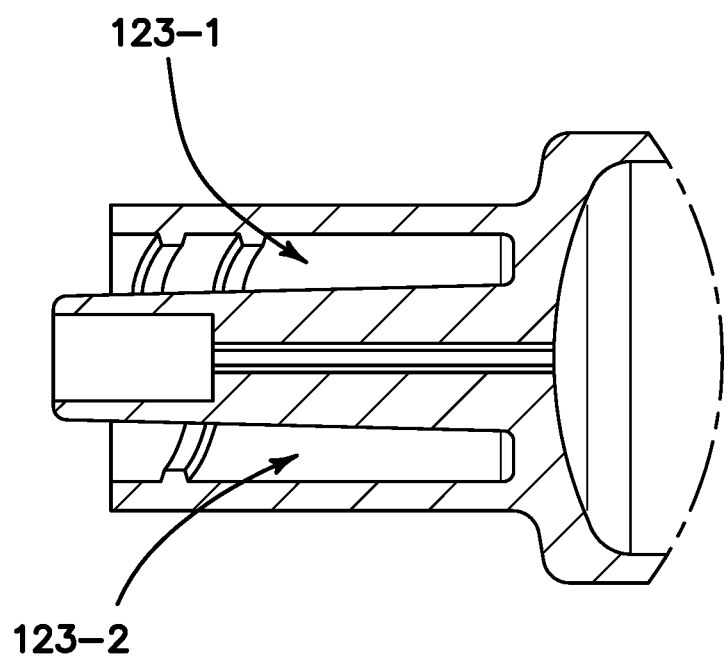
FIG. 22B illustrates a side view cross-sectional view of the syringe showing the side ports according to the embodiments of the present invention.
Figure 23A:
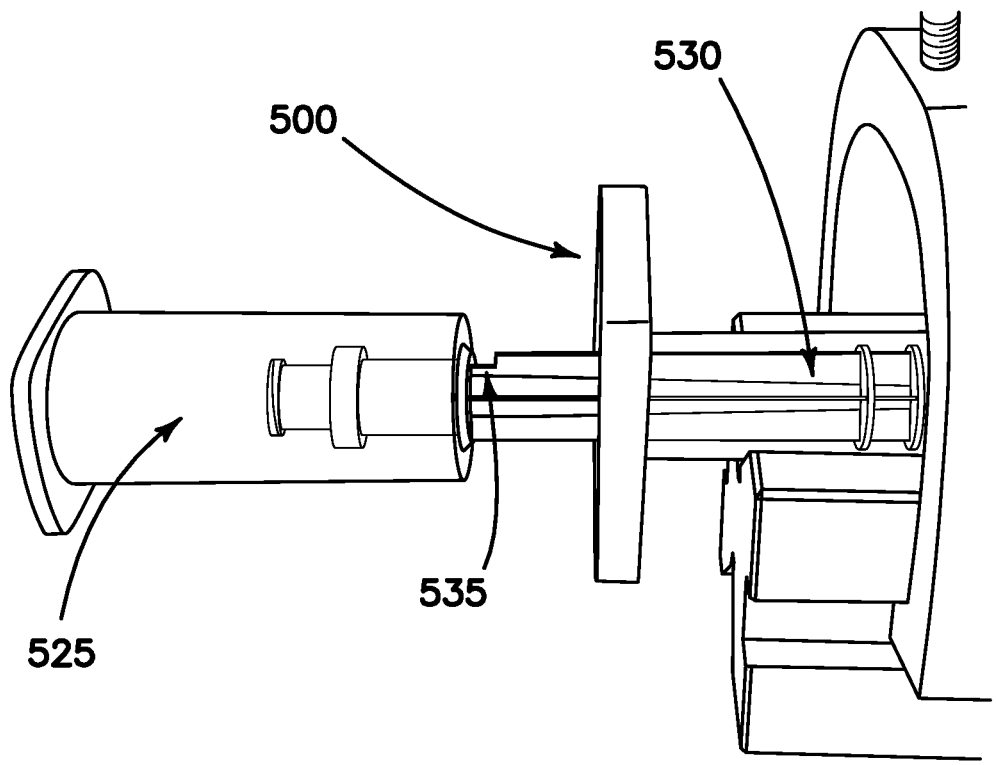
FIG. 23A illustrates a first view of an external locking mechanism according to the embodiments of the present invention.
Figure 23B:
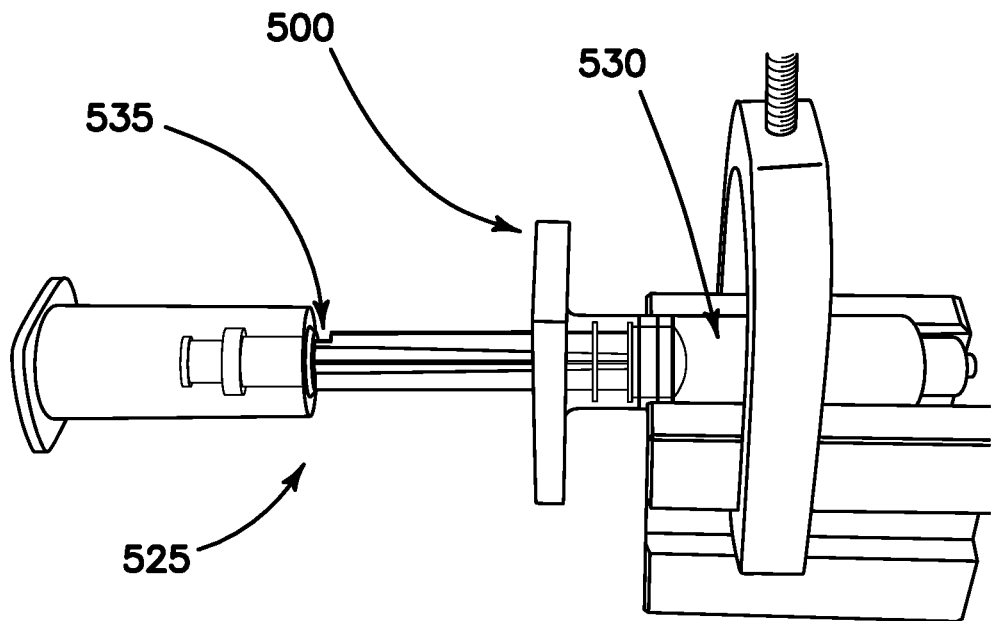
FIG. 23B illustrates a second view of an external locking mechanism according to the embodiments of the present invention.
Figure 23C:
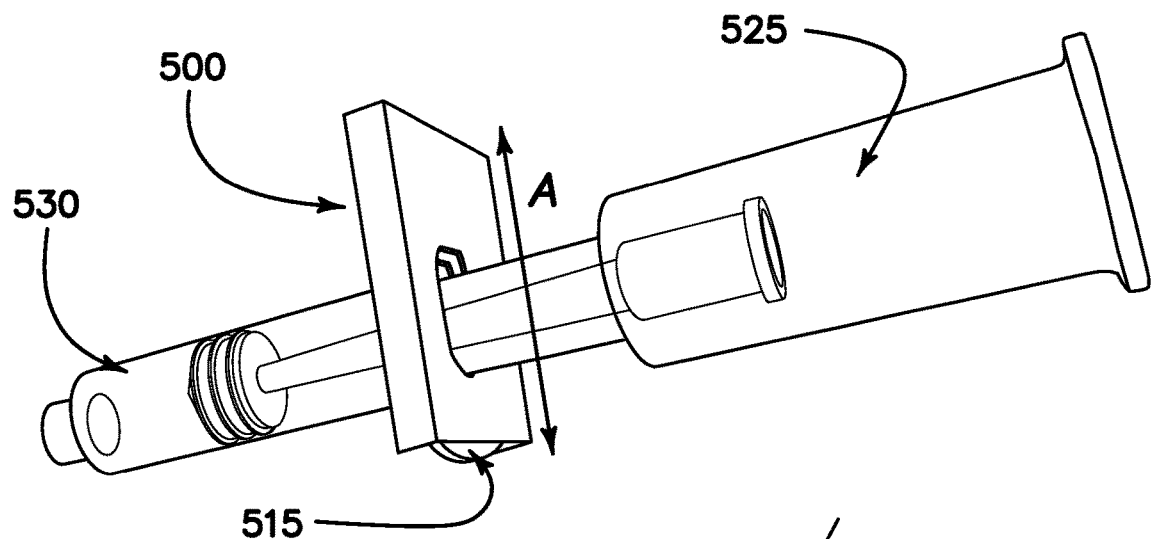
FIG. 23C illustrates a third view of an external locking mechanism according to the embodiments of the present invention.
Figure 23D:
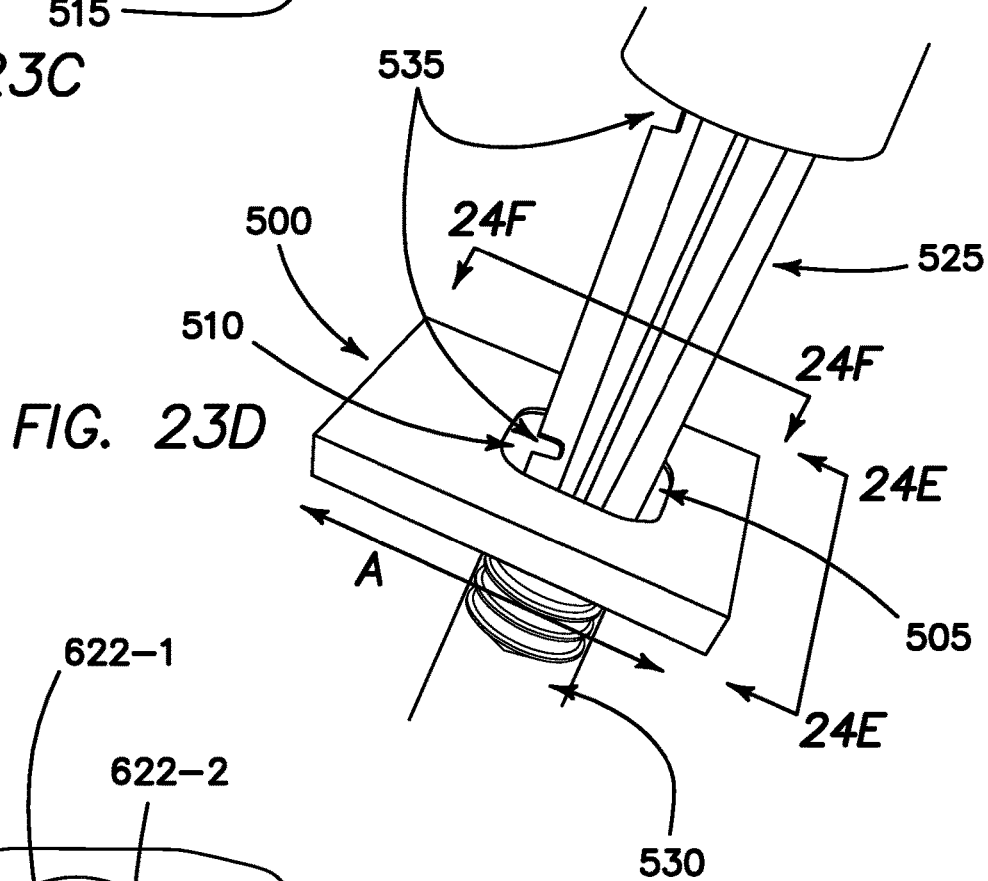
FIG. 23D illustrates a fourth view of an external locking mechanism according to the embodiments of the present invention.

In one embodiment, the syringe of the various syringe assemblies may be pre-filled with a flush, medicament or other fluid. In such an embodiment, the dimensions of side ports 123-1 and 123-2 as shown in FIGS. 22A and 22B are selected to provide a decreased pull pressure, prevent cell damage to ingested blood fluids, and facilitate pre-filling the fluid chamber. In other words, the size of the side ports 123, on either side of the central opening, is determined to permit proper fluid flow in and out of the syringe and may also provide means for pre-filling the syringe. The syringe can be filled utilizing a luer attached to the channel in the receiving cavity that receives a flush syringe. BY clamping the line, the contents when forced out of the flush syringe through the cannula into the clamped line are forced to back fill the syringe via the side ports. The contents of the syringe may now be used to flush the line. This again reduces the need to change or touch the main connection between the syringe assembly and the line into the patient.

FIGS. 23A-23F show an external locking mechanism 500 according to the embodiments of the present invention. The locking mechanism 500 includes an opening 505 and internal slot 510 to slide over the finger grip 515 of the syringe 530. The slot 510 (best seen in the cross-sectional views of FIGS. 23E and 23F) permits the locking mechanism 500 to slide (see arrow A) on the finger grip 515. Once in position, the opening 505 allows the plunger unit 525 to insert into the syringe 530. One or more cut-outs 535 in the plunger unit 525 serve to selectively lock the plunger unit 525 in place relative to the syringe 530 when an upper surface of the locking mechanism 500 defining the slot 510 is received by one of the cut-outs 535 thus locking the plunger unit 525 in place.

Figure 24A:
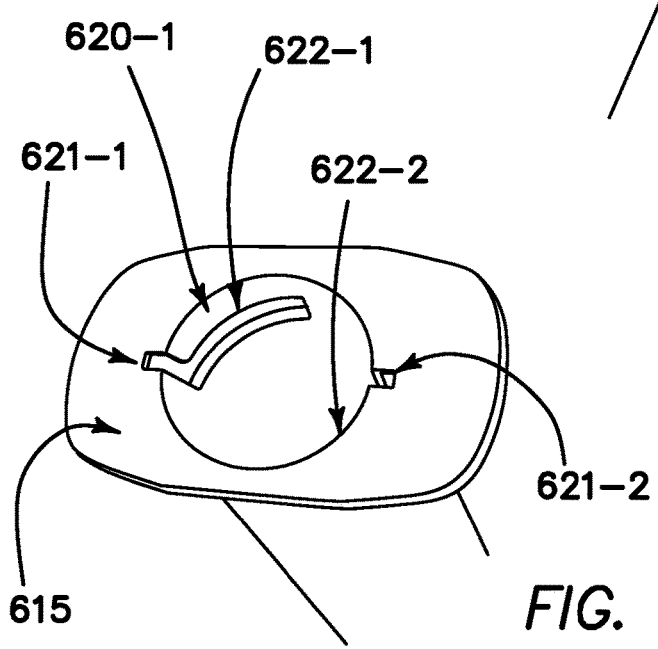
FIG. 24A illustrates a first view of an internal locking mechanism according to the embodiments of the present invention.
Figure 23E:
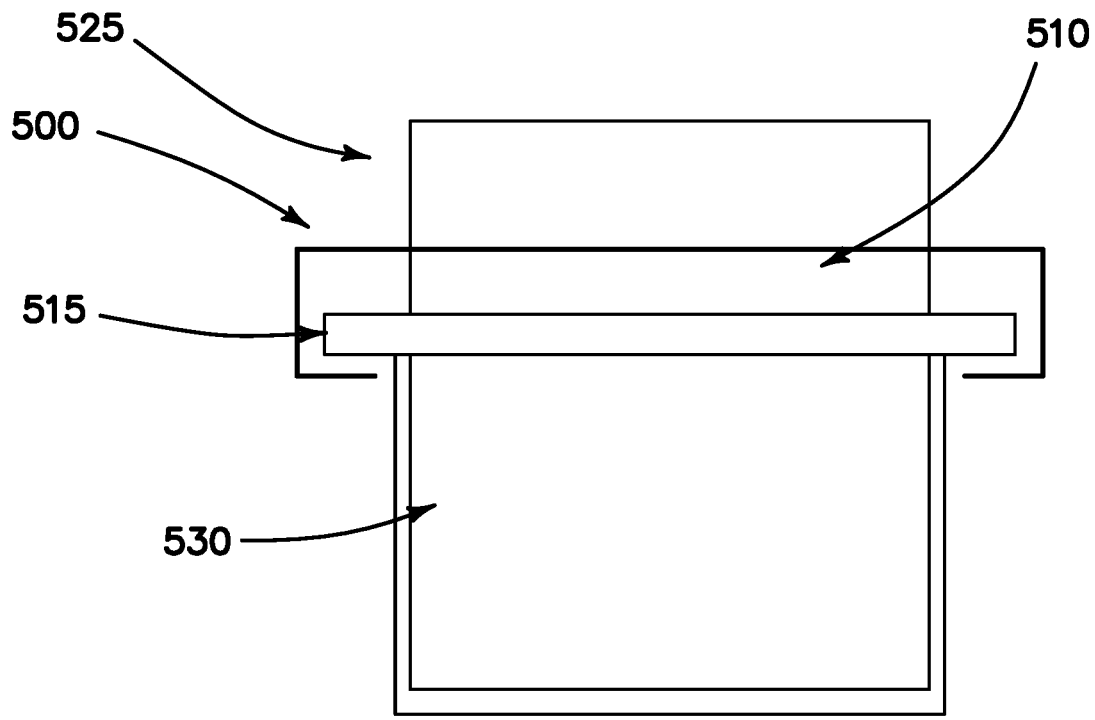
FIG. 23E illustrates a fifth view of an external locking mechanism according to the embodiments of the present invention.
Figure 23F:
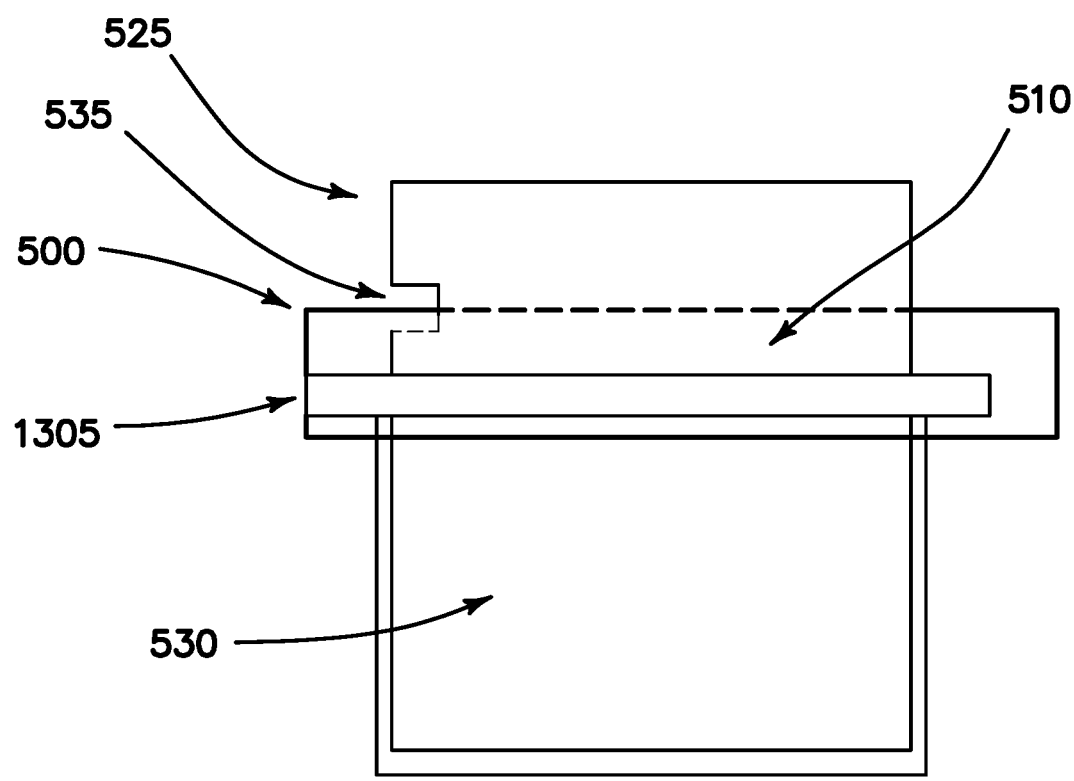
FIG. 23F illustrates a sixth view of an external locking mechanism according to the embodiments of the present invention.
Figure 24B:
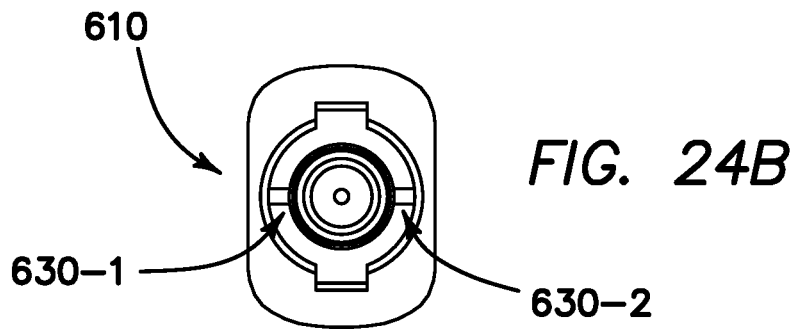
FIG. 24B illustrates a second view of an internal locking mechanism according to the embodiments of the present invention.
Figure 24C:
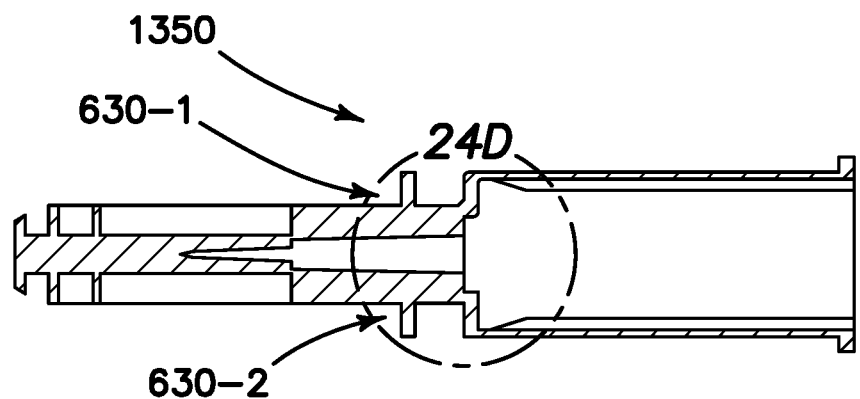
FIG. 24C illustrates a third view of an internal locking mechanism according to the embodiments of the present invention.
Figure 24D:
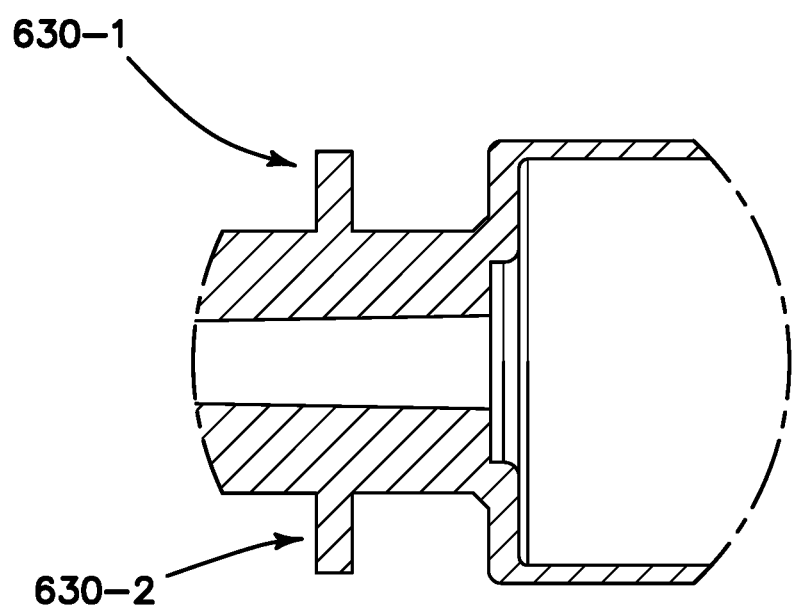
FIG. 24D illustrates a close view of flanges of an internal locking mechanism according to the embodiments of the present invention.

FIGS. 24A-24D show an integral locking mechanism according to the embodiments of the present invention. Locking mechanism locks the plunger unit 610 in place relative to the syringe 615. In this instance, the locking mechanism is formed in part on both the plunger unit 610 and the syringe 615. As best seen in FIG. 24A and the top view of FIG. 24B, the cylindrical body of the syringe 615 includes a pair of oppositely positioned slots 620-1 and 620-2 in a finger grip 625 thereof. A pair of projections or flanges 630-1 and 630-2 (best seen in FIGS. 24C and 24D) in the plunger unit 610 are configured and positioned to slide into upper segments 621-1 and 621-2 of the slots 620-1 and 620-2, respectively, and upon rotating the plunger unit 610, the projections 630-1 and 630-2 slide along the horizontal portions 622-1 and 622-2 of the slots 620-1 and 620-2 thereby locking the plunger unit 610 in position. Unlocking the plunger unit 610 comprises rotating the plunger unit 610 in the opposite direction and pulling the plunger unit 610 upward relative to the syringe 615.

In another embodiment, as shown in exaggerated fashion in FIGS. 24E and 24F, the cylindrical body 655 of the syringe 660 is tapered smaller away from the luer tip 665 so that the plunger unit 670 is effectively prevented from exiting the syringe 660 due to friction between the plunger unit piston 675 and inner wall of the cylindrical body 655 of the syringe 660. As designed and dimensioned, and as shown in FIG. 24F, the plunger unit piston 675 is able to reach near the top of the cylindrical body 655 with normal pull pressure by a user but ultimately the friction prevents further displacement (i.e., locks the plunger unit piston in position near the top opening of the syringe). While shown in a tapered configuration, the piston 675 may be circular or any other shape desired. In this embodiment, by locking the plunger unit 675 in a fully extended position, a vacuum is generated permitting the infusion of a medication (e.g., de-clotting agent) through a valve connected within the receiving cavity so that the vacuum draws the de-clotting agent into the clotted area within the catheter/central line or peripherally inserted central line (PICC).

Figure 25A:
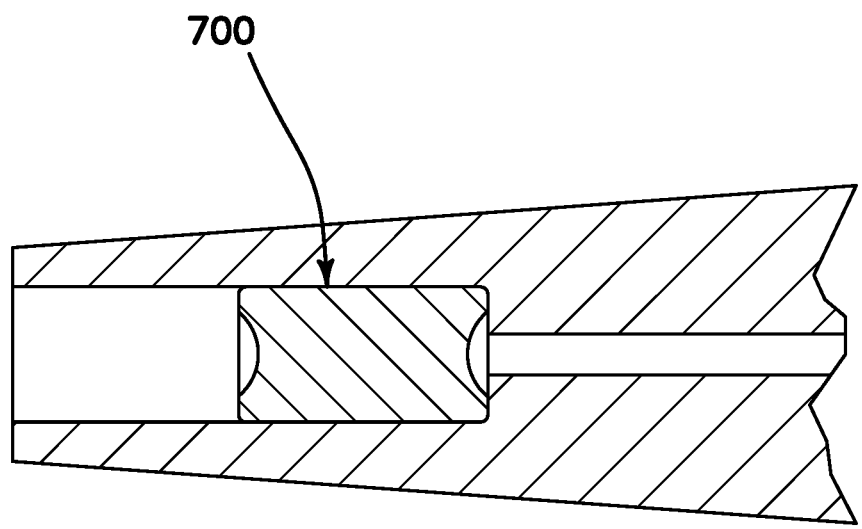
FIG. 25A illustrates a fluid de-accelerator insert positioned within a male luer tip according to the embodiments of the present invention.
Figure 25B:
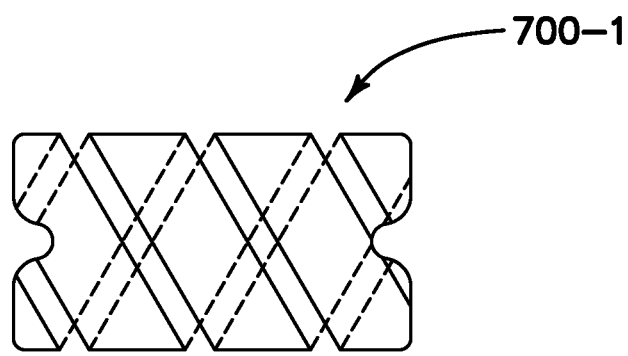
FIG. 25B illustrates a first fluid de-accelerator insert according to the embodiments of the present invention.
Figure 25C:
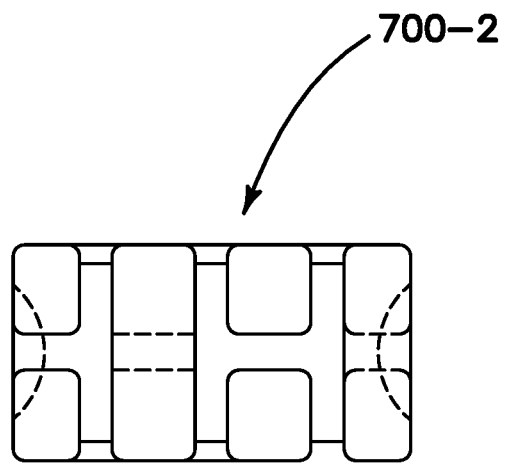
FIG. 25C illustrates a second fluid de-accelerator insert according to the embodiments of the present invention.

FIGS. 25A-25C show a fluid de-accelerator insert 700 according to the embodiments of the present invention. As shown, the fluid de-accelerator insert 700 can take on various shapes and dimensions. As shown in FIG. 25B, a first design 700-1 is a dual circuit double helix design. As shown in FIG. 25C, a second design 700-2 is a single circuit cross-over design. In either instance, the fluid de-accelerator insert 700 is positioned, as shown in FIG. 25A, within the luer of the syringe assembly proximate the secured cannula. The insert serves to control fluid flow into and out of the syringe via side ports. As fluid passes about the circumferences of the inserts it is slowed by the various path designs. Those skilled in the art will recognize that other designs are conceivable.

Figure 26:
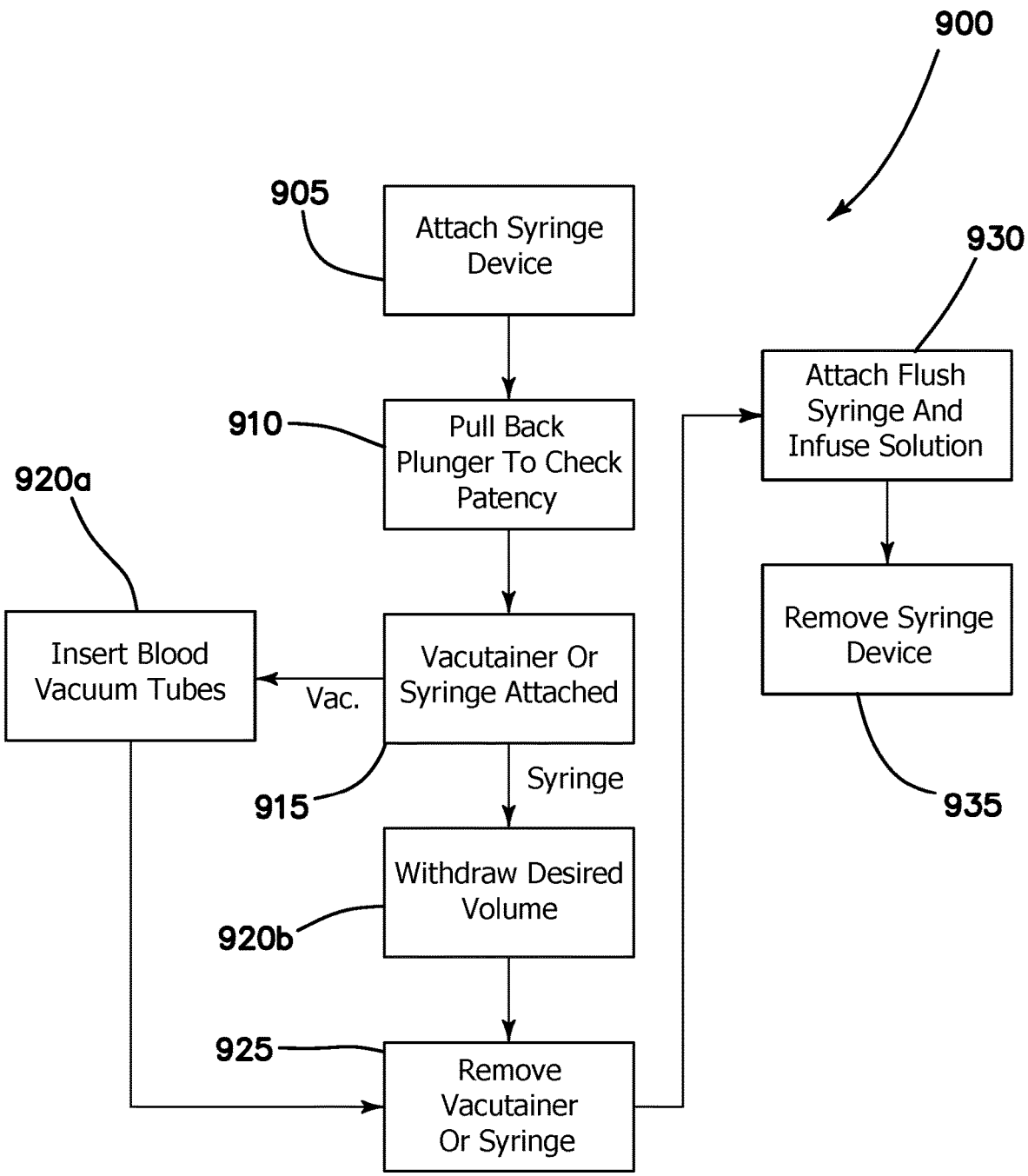
FIG. 26 illustrates a first method facilitated by the syringe assembly embodiments of the present invention.

The embodiments of the present invention facilitate a series of methods. A first method detailed in flow chart 900 of FIG. 26 relates to a single IV/arterial access closed system blood collection system. This system reduces multiple accesses to a catheter connector to a single access. In this embodiment, the syringe includes access for insertion of a vacutainer holder to withdraw blood. At 905, attach the syringe assembly according to the embodiments of the present invention to a catheter or IV connector on a catheter or Y site access. At 910, a plunger unit is pulled back to aspirate and draw Heparin or blood or medications into the syringe chamber to clear the catheter (i.e., check patency). At 915, a vacutainer or syringe is attached by rotating and locking onto the valve in the receiving cavity. At 920A, if utilizing a vacutainer, insert blood collection vacuum tubes to obtain samples or, at 920B, if utilizing a syringe, use the syringe to withdraw until a desired volume is achieved. At 925, remove the vacutainer or syringe and re-infuse Heparin or blood or medications into patient. At 930, attach a flush syringe and infuse per facility protocol. At 935, remove syringe from patient and discard per hospital protocol.

Figure 27:
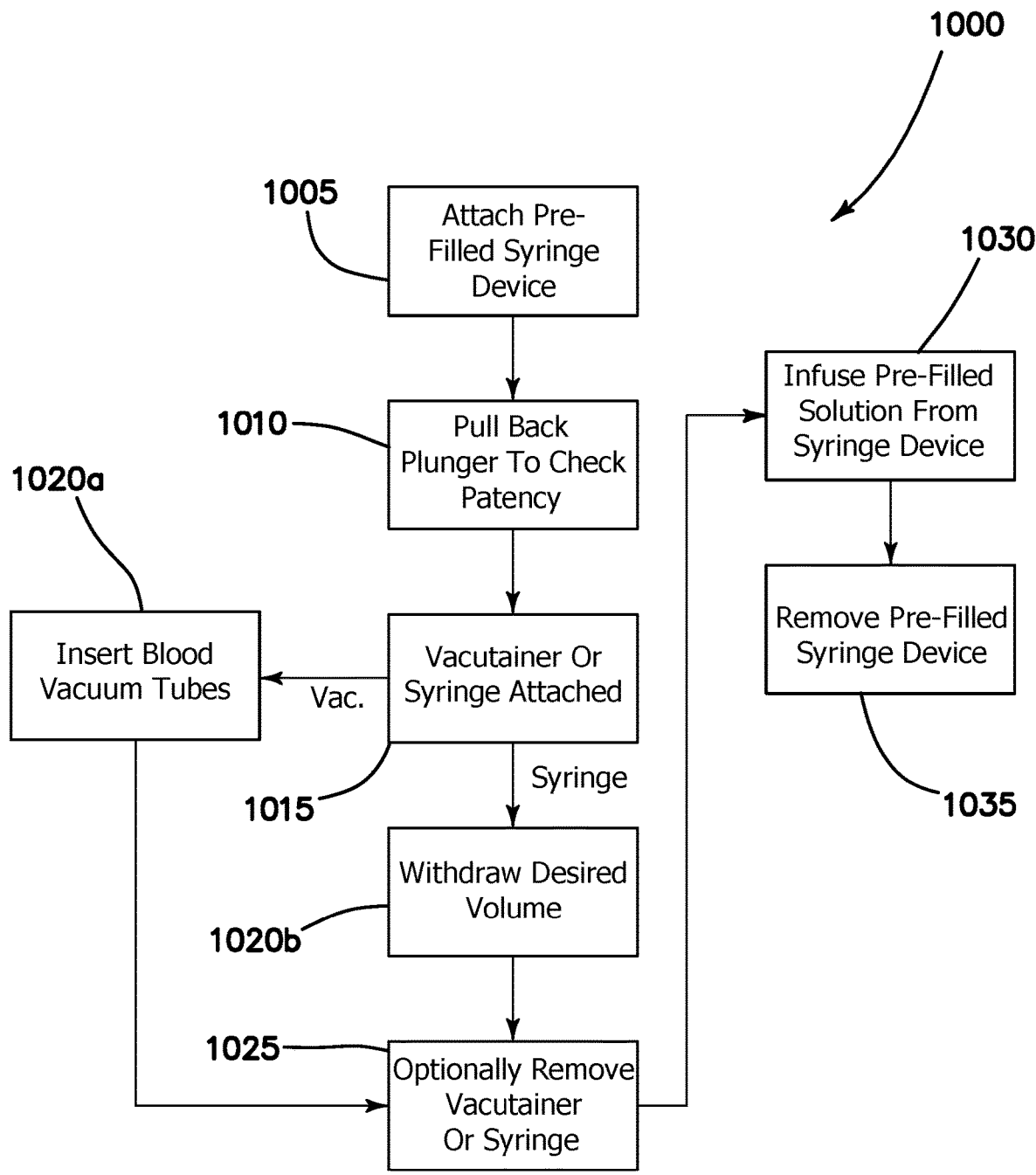
FIG. 27 illustrates a second method facilitated by the syringe assembly embodiments of the present invention.

A second method detailed in flow chart 1000 of FIG. 27 relates to a syringe assembly pre-filled with a flush solution. At 1005, attach the syringe assembly according to the embodiments of the present invention to a catheter or IV connector on a catheter or Y site access. At 1010, check patency by pulling back on plunger unit. At 1015, a vacutainer or syringe is attached by rotating and locking onto the valve. At 1020A, if utilizing a vacutainer, insert blood collection vacuum tubes to obtain samples or at 1020B, if utilizing a syringe, use the syringe to withdraw until a desired volume is achieved. At 1025, optionally remove the vacutainer or syringe. At 1030, depress plunger unit to infuse pre-filled flush solution. At 1035, remove syringe from patient and discard per hospital protocol.

The versatility of the syringe assembly according to the embodiments of the present invention permits aspiration and administration with any needleless connector and any closed system transfer device utilizing male/female components thus bypassing steps that are subject to user variances and exposure to a growing list of hazardous drugs. The syringe assemblies according to the embodiments of the present invention are ideal for handling hazardous drugs because the syringe assemblies are compatible with all needleless connectors, all female luer hubs (e.g., peripheral IV catheters, single, double and triple lumen lines, stopcocks and manifolds, T-connectors, etc.), needle free connectors, intravenous push of hazardous drugs, syringes containing a hazardous drug with a closed system transfer device can be safely disconnected from a mating needleless connector allowing a flush to be connected for a complete intravenous drug push.

The syringe assemblies according to the embodiments of the present invention (i) may be used with all needle free connectors, catheters and closed system transfer devices; (ii) provide single access that prevents design related contamination of the needle free connector known to increase with multiple accesses (can help hospitals achieve optimal central line associated blood stream infection; (iii) validate patency during hazardous drug administration; and (iv) prevent hazardous drug exposure by eliminating intravenous push administration of hazardous drugs that require immediate flush to ensure complete dose is flushed and line is clear of blood.

Single access minimizes potential contamination to the internal structure of the valve resulting in multiple changes or risks to central line associated blood stream infection rates which affect hospital CMS reimbursement. The current procedure comprises (i) disinfect; (ii) access with flush syringe; (iii) de-access; (iv) disinfect; (v) attach medication; (vi) detach; (vii) disinfect; (viii) attach flush; (ix) detach disinfect; (x) attach lock and (xi) detach. With current invention the procedure comprises: (i) disinfect; (ii) attach; (iii) utilize as needed and (iv) detach.

Moreover, the instant syringe assemblies accommodate administration of hazardous drugs in compliance with USP800 regulations because it is compatible with all needleless connector components and any female luer hubs, needle free connectors and closed system transfer devices may be added for safe transport, patency check and intravenous push of hazardous drugs, syringes containing hazardous drugs with a closed system transfer device can be safely disconnected from mating needleless connector, flush syringe can then be applied for complete delivery of intravenous push medication and safe removal of the syringe system.

Figure 28:
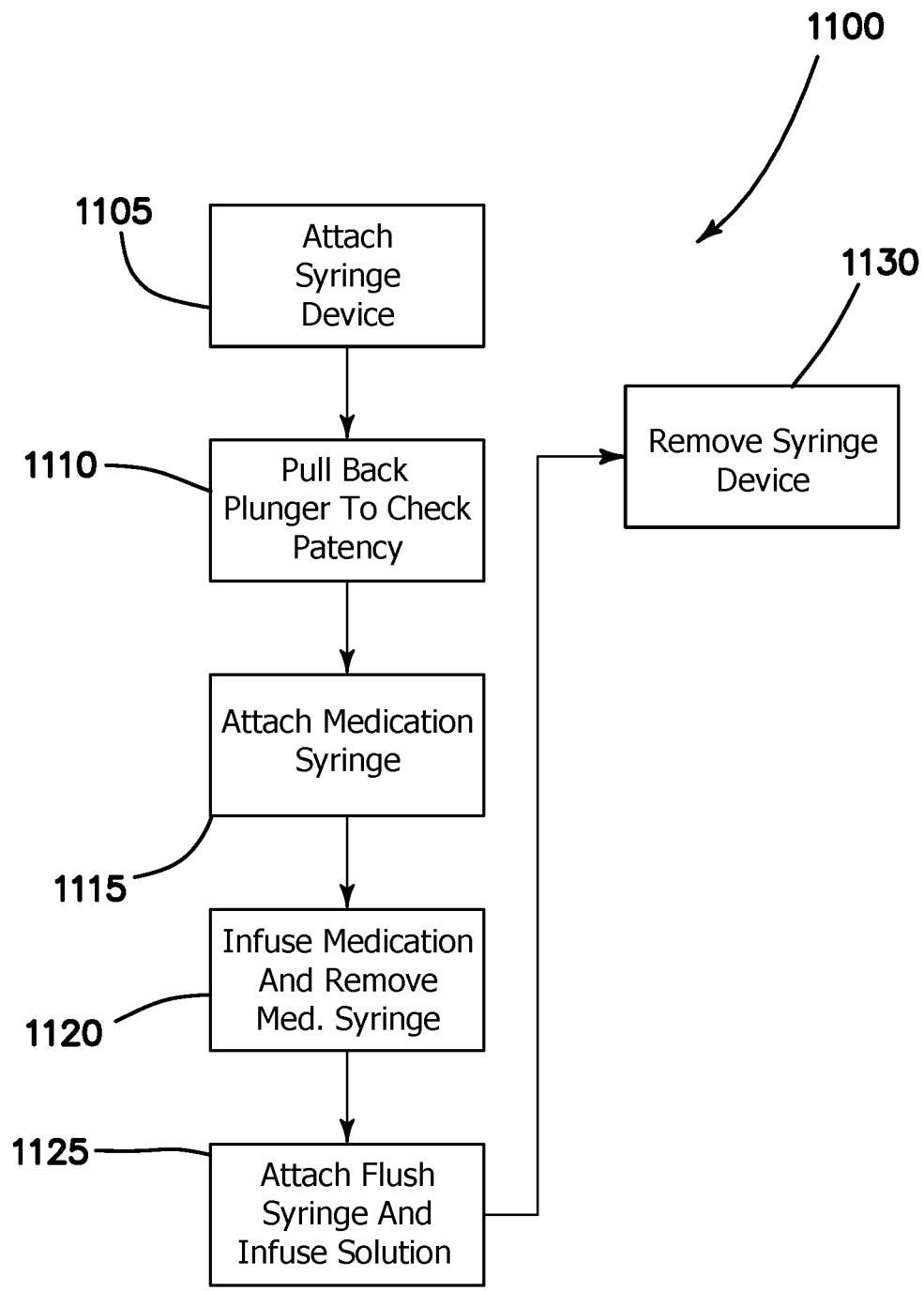
FIG. 28 illustrates a third method facilitated by the syringe assembly embodiments of the present invention.

A third method detailed in flow chart 1100 of FIG. 28 relates to single access for drug administration including hazardous agents. At 1105, attach the syringe assembly according to the embodiments of the present invention to a catheter or IV connector on a catheter or Y site access. At 1110, check patency by pulling back on plunger unit. At 1115, attach medication syringe (with or without closed male luer) to plunger unit. At 1120, infuse medication and remove syringe assembly. At 1125, attach flush syringe and infuse flush solution. At 1030, remove syringe assembly from patient and discard per hospital protocol.

Figure 29:
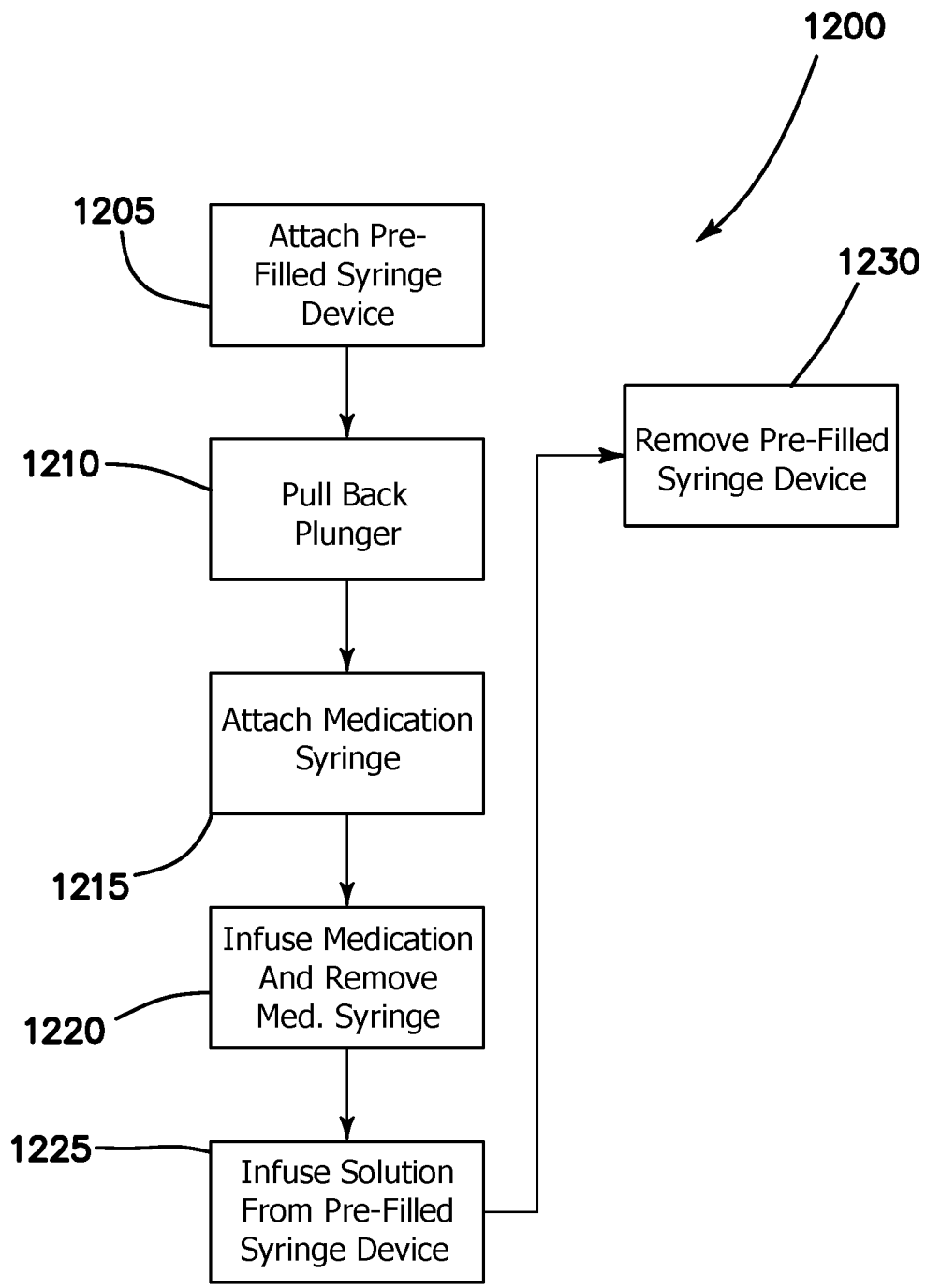
FIG. 29 illustrates a fourth method facilitated by the syringe assembly embodiments of the present invention.

A fourth method detailed in flow chart 1200 of FIG. 29 relates to syringe assembly pre-filled with a flush solution. At 1205, attach the syringe assembly according to the embodiments of the present invention to a catheter or IV connector on a catheter or Y site access. At 1210, check patency by pulling back on plunger unit. At 1215, attach medication syringe (with or without closed male luer) to plunger unit. At 1220, infuse medication and remove syringe assembly. At 1225, infuse flush solution. At 1230, remove syringe assembly from patient and discard per hospital protocol.

In one embodiment of the present invention, the syringe assembly is manufactured by first assembling the syringe, plunger unit and piston into a unit and then mechanically inserting the cannula into place through the piston at a first end and proximate a syringe tip opening at a second end. Such a process is more efficient and creates a more stable product.

The embodiments of the present invention serve to minimize contamination risks by using a closed vascular system. Such systems minimize the potential for cross-contamination and touch-contamination (e.g., human factor during access/de-access) and potential contamination to the internal structure of the valve (e.g., design flaws). The rates associated with such contamination affects hospital CMS reimbursement. By utilizing the pre-filling feature (saline or other fluid) of the embodiments of the present invention, multiple accesses and/or steps to disinfect the valve can be eliminated. By reducing access and de-access steps, exposure of the threads and internal compartments is eliminated making a single disinfection adequate prior to line procedures. This is accomplished because the syringe luer remains engaged and allows the flush solution to expel the blood from the valve prior to removal of the syringe. This eliminates the opening and reinsertion of a flush syringe thus preventing the blood and particulate from finding its way into the nooks and crannies of the mating valve on either a peripheral or central line. This will greatly reduce blood borne pathogen exposure and reduce the potential for BSI's/CLBSI's.

In one embodiment, the syringe of the embodiments of the present invention are compatible with culture bottle and sterile collection devices that effectively remove potentially contaminated skin flora in a waste cavity. In other words, routine blood collection can be standardized to include a culture specimen with the syringe as detailed herein.

In an embodiment having an interface for receipt of a vacutainer in the receiving cavity, the rubber seal or condom which prevents the flow of air into the needle of a multi-sample luer adapter is modified such that the rubber seal includes a thicker wall near the base or a skirt to provide an improved air tight seal.

Figure 30A:
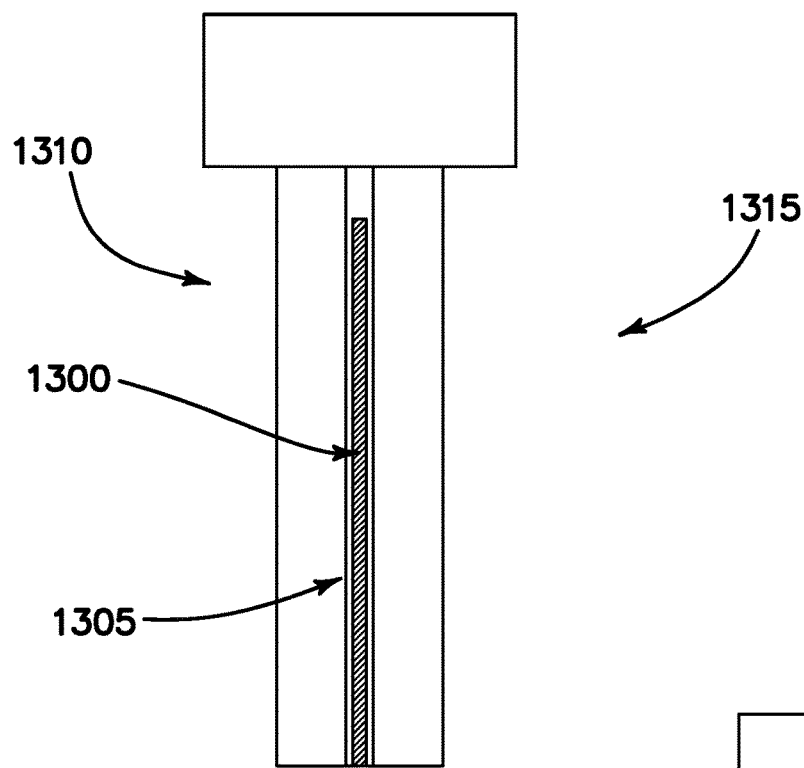
FIG. 30A illustrates a first means for reducing fluid entering into a plunger unit channel according to the embodiments of the present invention.
Figure 30B:
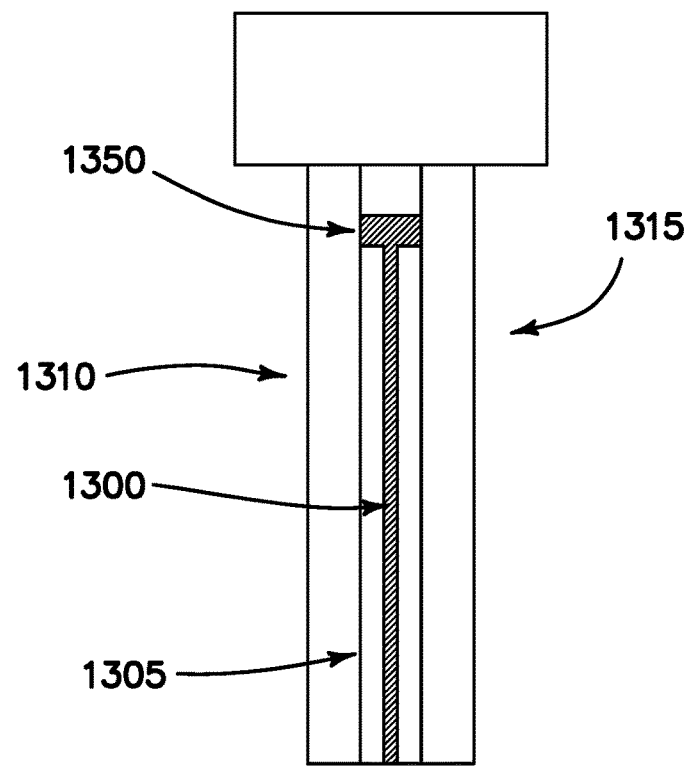
FIG. 30B illustrates a second means for reducing fluid entering into a plunger unit channel according to the embodiments of the present invention.

In another embodiment, as shown in FIGS. 30A and 30B, means for preventing fluids exiting the cannula 1300 into the channel 1305 of the adapter portion 1310 of the plunger unit 1315 are incorporated into the syringe assembly design. In one embodiment, shown in FIG. 30A, the channel 1305 is fabricated with such tolerances to minimize the volume between the outer surface of the cannula 1300 and the inner surface of the channel 1305. In another embodiment, shown in FIG. 30B, an O-ring 1350 is attached to the top of the cannula 1300 prevents fluids from seeping below into the depths of the channel 1305. In other embodiments, the channel 1305 may receive an internal sleeve with a wiper seal, overmold seal on the plunger unit, drop-in insert, etc. In one embodiment, the sleeve or insert extends from the luer tip to the channel opening in the receiving cavity. Reducing the available volume in the channel is important when infusing micro/small doses of medication and subsequent flushing.

Although the invention has been described in detail with reference to several embodiments, additional variations and modifications exist within the scope and spirit of the invention as described and defined in the following claims.

We claim:

1. A syringe assembly comprising:
a syringe including a cylindrical body with a luer at a first end, said luer including an exit opening;
a plunger unit including an adapter portion and a receiving cavity, a first end of said adapter portion retaining a piston, said plunger unit insertable into a second end of said syringe and slidable within said cylindrical body during which said piston creates a fluid seal with an interior surface of said cylindrical body, said adapter portion including a channel extending along a length of said adapter portion to an opening at a bottom of said receiving cavity, said receiving cavity for insertion of an intermediary connector or valve; and
a cannula attached to an inner surface of a luer tip and extending into said piston and extendable into said channel as said plunger unit is inserted farther into said syringe, said cannula attached to an inner surface of said luer tip so that said cannula is recessed from said exit opening of said luer tip to accommodate attachment of connectors into said exit opening, attachment of said cannula to said inner surface of said luer tip not preventing fluid flow between said luer tip and said cylindrical body.

2. The syringe assembly of claim 1 wherein said cannula is recessed from said luer tip opening in a range of 0.15 inches to 0.35 inches.

3. The syringe assembly of claim 1 wherein said cylindrical body is pre-filled with a flush, medicament or other fluid.

4. The syringe assembly of claim 1 further comprising means for preventing fluid from exiting said cannula into said channel.

5. The syringe assembly of claim 1 wherein said receiving cavity has a depth in a range of 1 inch to 1.5 inches.

6. A syringe assembly comprising:
a syringe including a cylindrical body with a luer at a first end, said luer including an exit opening;
a plunger unit including an adapter portion and a receiving cavity, a first end of said adapter portion retaining a piston, said plunger unit insertable into a second end of said syringe and slidable within said cylindrical body during which said piston creates a fluid seal with an interior surface of said cylindrical body; and
a cannula attached to an inner surface of a luer tip and extending into said piston and extendable into said channel as said plunger unit is inserted farther into said syringe, said cannula attached to an inner surface of said luer tip so that said cannula is recessed from said exit opening of said luer tip to accommodate attachment of connectors into said exit opening, attachment of said cannula to said inner surface of said luer tip not preventing fluid flow between said luer tip and said cylindrical body.

7. The syringe assembly of claim 6 wherein said cannula is recessed from said luer tip opening in a range of 0.15 inches to 0.35 inches.

8. The syringe assembly of claim 7 wherein said receiving cavity has a depth in a range of 1 inch to 1.5 inches.

9. The syringe assembly of claim 7 wherein said adapter portion includes a channel extending along a length of said adapter portion to an opening at a bottom of said receiving cavity, said receiving cavity for insertion of an intermediary connector or valve.

10. A syringe assembly comprising:
a syringe including a cylindrical body with a luer at a first end, said luer including an exit opening;
a plunger unit including an adapter portion and a receiving cavity, a first end of said adapter portion retaining a piston, said plunger unit insertable into a second end of said syringe and slidable within said cylindrical body during which said piston creates a fluid seal with an interior surface of said cylindrical body;
a cannula attached to an inner surface of a luer tip and extending into said piston and extendable into said channel as said plunger unit is inserted farther into said syringe, said cannula attached to an inner surface of said luer tip so that said cannula is recessed from said exit opening of said luer tip, attachment of said cannula to said inner surface of said luer tip not preventing fluid flow between said luer tip and said cylindrical body;

a connecter including a spike; and wherein a space created by said recessed cannula sand said luer tip accommodates attachment of said connector into said exit opening.

11. The syringe assembly of claim 10 wherein said cannula is recessed from said luer tip opening in a range of 0.15 inches to 0.35 inches.

12. The syringe assembly of claim 10 further comprising means for preventing fluid from exiting said cannula into said channel.

13. The syringe assembly of claim 10 wherein said receiving cavity has a depth in a range of 1 inch to 1.5 inches.

14. The syringe assembly of claim 10 wherein said adapter portion includes a channel extending along a length of said adapter portion to an opening at a bottom of said receiving cavity, said receiving cavity for insertion of an intermediary connector or valve.

15. The syringe assembly of claim 1 wherein said cannula is attached to said inner surface of said luer tip using one or more flanges, struts, wings and/or adhesives.

16. The syringe assembly of claim 6 wherein said cannula is attached to said inner surface of said luer tip using one or more flanges, struts, wings and/or adhesives.

17. The syringe assembly of claim 10 wherein said cannula is attached to said inner surface of said luer tip using one or more flanges, struts, wings and/or adhesives.

* * * * *